United States Patent
Hong et al.

(10) Patent No.: US 10,422,775 B2
(45) Date of Patent: Sep. 24, 2019

(54) METHODS FOR DETERMINING RELATIVE RESPONSE FACTORS FOR IMPURITY ANALYSIS USING LIQUID CHROMATOGRAPHY WITH ABSORBANCE AND EVAPORATIVE LIGHT SCATTERING DETECTION

(71) Applicant: Waters Technologies Corporation, Milford, MA (US)

(72) Inventors: Paula Hong, Ashland, MA (US); Michael D. Jones, Narragansett, RI (US)

(73) Assignee: Waters Technologies Corporation, Milford, MA (US)

( * ) Notice: Subject to any disclaimer, the term of this patent is extended or adjusted under 35 U.S.C. 154(b) by 331 days.

(21) Appl. No.: 15/404,851

(22) Filed: Jan. 12, 2017

(65) Prior Publication Data
US 2017/0199166 A1    Jul. 13, 2017

Related U.S. Application Data

(60) Provisional application No. 62/277,789, filed on Jan. 12, 2016.

(51) Int. Cl.
| | |
|---|---|
| *G01N 30/06* | (2006.01) |
| *G01N 30/86* | (2006.01) |
| *G01N 30/74* | (2006.01) |
| *G01N 33/15* | (2006.01) |
| *G01N 30/88* | (2006.01) |
| *G01N 30/02* | (2006.01) |
| *G01N 30/04* | (2006.01) |

(52) U.S. Cl.
CPC ............. *G01N 30/06* (2013.01); *G01N 30/74* (2013.01); *G01N 30/8624* (2013.01); *G01N 30/8631* (2013.01); *G01N 30/8641* (2013.01); *G01N 30/8665* (2013.01); *G01N 30/8679* (2013.01); *G01N 33/15* (2013.01); *G01N 2030/027* (2013.01); *G01N 2030/045* (2013.01); *G01N 2030/8872* (2013.01)

(58) Field of Classification Search
CPC .......... G01N 30/8631; G01N 30/8641; G01N 30/8665; G01N 30/8624; G01N 30/8679; G01N 2030/8872; G01N 33/15
See application file for complete search history.

(56) References Cited

PUBLICATIONS

Young, Craig et al. "Success with Evaporative Light-Scattering Detection" LC GC Europe, Mar. 2003. (Year: 2003).*
(Continued)

*Primary Examiner* — Paul M. West
(74) *Attorney, Agent, or Firm* — Womble Bond Dickinson (US) LLP; Deborah M. Vernon; Rebecca Barnes

(57) ABSTRACT

Methods and systems for determining relative response factors for liquid chromatography using both molar concentration-based detection and mass concentration-based detection are described herein. A method includes determining a relative response factor for a compound based on the ratio of a molar-based peak area for the compound to the logarithm of the mass-based peak area for the compound and based on the ratio of a molar-based peak area for a reference compound divided by the logarithm of the mass-based peak area for the reference compound.

24 Claims, 27 Drawing Sheets

(56) References Cited

PUBLICATIONS

Baertschi, Stephen W. "Assessing mass balance in pharmaceutical drug products: New insights into an old topic," Trends in Analytical Chemistry 49 (Sep. 2013) pp. 126-136.

Nussbaum, Mark A. "Role of 'mass balance' in pharmaceutical stress testing," Pharmaceutical Stress Testing: Predicting Drug Degradation, Ed. Stephen W. Bertschi, 2nd Edition, CRC Press 2011, pp. 233-253. (The month of publication is not available; however, the year of publication is sufficiently earlier than the affective U.S. filing date and any foreign priority date so that the particular month of publication is not an issue.).

Sowjanya, Prathyusha. "Novel validated stability-indicating UPLC method for determination of Metoclopramide and its degradation impurities in API and pharmaceutical dosage form," Journal of Pharmacy Research 6 (Jul. 2013) pp. 765-773.

\* cited by examiner

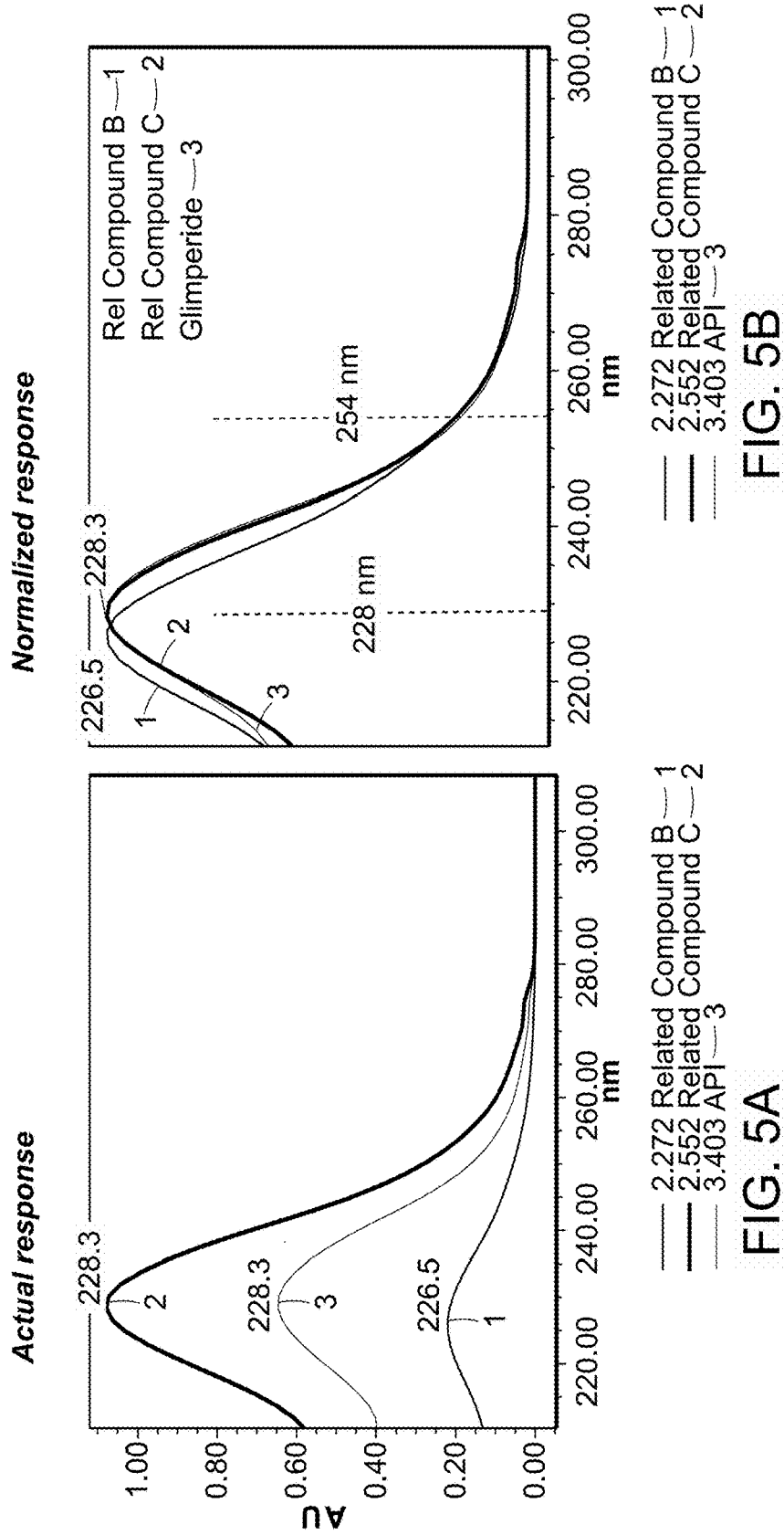

Correction Factor

| | Name | Component Type | Retention Time (min) | RT Window (min) | Peak Match | Impurity RRF |
|---|---|---|---|---|---|---|
| 1 | GlimepirideB | Low Level Impurity | 0.402 | 0.150 | Closest | 0.7300 |
| 2 | GlimepirideC | Low Level Impurity | 0.551 | 0.149 | Closest | 0.9000 |
| 3 | Glimepiride | Main Component | 2.961 | 0.149 | Closest | 1.0000 |

Corrected PDA Peak Area

| Name | Retention Time (min) | Area (μV*sec) | % Area | Height (μV) | Int Type | Relative Response | Corrected Area (μV*sec) | % Adjusted Area |
|---|---|---|---|---|---|---|---|---|
| GlimepirideB | 0.380 | 4612 | 0.24 | 4603 | BV | 0.730000 | 3367 | 0.172 |
| GlimepirideC | 0.544 | 740 | 0.04 | 596 | BB | 0.900000 | 666 | 0.034 |
| Glimepiride | 2.942 | 1956638 | 99.73 | 363371 | BB | 1.000000 | 1956638 | 99.794 |

FIG. 10

|  | Ref | D-0 | D1 | D3 | D5 | D7 |
|---|---|---|---|---|---|---|
| Injection 1 | 1976722 | 1974032 | 1989154 | 2026604 | 1998321 | 2035059 |
| Injection 2 | 1988436 | 1961001 | 1992650 | 2021903 | 1994358 | 2041720 |
| Injection 3 | 1989218 | 1961961 | 1989450 | 2021813 | 1995373 | 2044402 |
| Average | 1984792 | 1965665 | 1990418 | 2023440 | 1996017 | 2040394 |

|  | Origin/calculation | Ref | D-0 | D1 | D3 | D5 | D7 |
|---|---|---|---|---|---|---|---|
| Average Peak area | From Empower | 1984792 | 1965665 | 1990418 | 2023440 | 1996017 | 2040394 |
| mg(using corrected area) | Based on calibration curve in Empower | 237.9 | 235.6 | 238.5 | 242.5 | 239.2 | 244.5 |
| AMBD (grams)- Absolute Mass Balance Deficit | mg ref-mg degraded sample |  | 2.3 | -0.7 | -4.6 | -1.3 | -6.7 |
| % recovery | (Average Area degraded sample/Average Area reference sample )*100 |  | 99.0 | 100.3 | 101.9 | 100.6 | 102.8 |
| Average area of API | From Empower |  | 1961039 | 1943000 | 1890382 | 1766083 | 1712576 |
| %API | (Average Area API/Average Area total)*100 |  | 99.8 | 97.6 | 93.4 | 88.5 | 83.9 |
| % Impurities | 100-%API |  | 0.2 | 2.4 | 6.6 | 11.5 | 16.1 |

FIG. 11

METHODS FOR DETERMINING RELATIVE RESPONSE FACTORS FOR IMPURITY ANALYSIS USING LIQUID CHROMATOGRAPHY WITH ABSORBANCE AND EVAPORATIVE LIGHT SCATTERING DETECTION

RELATED APPLICATION

This application claims priority to and benefit of U.S. Provisional Patent Application No. 62/277,789, entitled "Methods for Determining Relative Response Factors for Impurity Analysis using Liquid Chromatography with Absorbance and Evaporative Light Scattering Detection," filed Jan. 12, 2016, which is incorporated by reference herein in its entirety.

TECHNICAL FIELD

The present disclosure generally relates to the methods for determining relative response factors for compounds in chromatographic analysis using molar concentration-based detection combined with mass concentration-based detection.

BACKGROUND

Drug products and drug substances undergo forced degradation studies in which the stability of the drug substances and drug products are tested under extreme conditions to understand the degradation pathway of the active pharmaceutical ingredient (API), and to understand which impurities are degradation products and which are non-drug related. In such studies, mass balance is critical to understand degradation pathways and to ensure all impurities are accounted for. Mass balance is the practical application of the Law of Conservation of Mass, the total mass of the reactants consumed must equal the total mass of products formed, to chemical synthesis and degradation. With respect to drug stability and associated analyses, the International Conference on Harmonization (ICH) defines mass balance as "the process of adding together the assay value and levels of degradation products to see how closely these add up to 100% of the initial value, with due consideration of the margin of analytical error." During a forced degradation study, impurities, specifically degradation products, must be summarized and measured relative to the API. When measuring the composition of the degraded sample using a chromatographic analysis system, the responsiveness of the detector of the analysis system to the API may be different than the responsiveness of the detector to the impurities. This can result in erroneous results for measurements of the concentrations of the impurities leading to corresponding errors in recovery for the mass balance.

One technique used to correct for differences in detector responsiveness to the API and to impurities involves generating calibration curves for the API and each impurity on the analytical system using samples with known concentrations of the API and of each impurity (e.g., known concentrations of standards). In a calibration curve, the slope of the detector response versus concentration is determined for each compound (e.g., for the API and for each impurity). This slope is referred to as the response factor for the compound. A relative response factor can be calculated for each impurity as the response factor of the impurity divided by the response factor of the API. This relative response factor can then be used to correct for the difference in detector responsiveness between the API and the impurities. Because the relative response factors are dependent on the specifics of the chromatographic method employed (e.g., column, gradient, mobile phases, etc.), the same conditions used for determining the RRF should be used for the subsequent mass balance analysis. Although this calibration curve-based technique for determining a relative response factor is well established and reliable, standards of known concentrations of the impurities are not always available. This calibration curve-based technique for determining relative response factors is also time-consuming as it requires measuring multiple different samples with known concentrations of the API and impurities to generate the calibration curves. Another technique of correcting for differences in detector responsiveness to the API and to impurities involves isolating the impurities from a sample and then using the impurities as standards when generating the calibration curves.

Nuclear magnetic resonance (NMR) may be used to determine relative response factors to correct for differences in detector responsiveness. NMR is nearly universal, quantitative on a molar basis, and well-established; however, it has numerous drawbacks (e.g., it is expensive and only detects compounds in relatively high concentrations). Further, it requires unique proton resonances and may not distinguish between closely related molecules.

Given the importance of stability studies for pharmaceuticals and accurate quantification of amounts of APIs and impurities, there is a need for a method of determining relative response factors for detection of substances in chromatographic separation that is not subject to the disadvantages described above.

SUMMARY

In general, the present disclosure relates methods of determining relative response factors (RRFs) using molar concentration-based detection and mass-concentration based detection methods and methods of mass balance employing such relative response factors.

In one aspect, a method for determining relative response factors includes performing liquid chromatographic separation of a sample including a reference compound and one or more additional compounds. The method also includes performing molar concentration-based detection on the separated sample to determine a molar-based peak area for the reference compound and for each of the one or more additional compounds. The method includes performing mass concentration-based detection on the separated sample to determine a mass-based peak area for the reference compound and for each of the one or more additional compounds. The method also includes determining a relative response factor (RRF) for each of the one or more additional compounds based on the ratio of the molar-based peak area for the additional compound to the logarithm of the mass-based peak area for the additional compound and the ratio of the molar-based peak area for the reference compound to the logarithm of the mass-based peak area for the reference compound.

In another aspect, a method for determining relative response factors includes performing liquid chromatographic separation of a first sample including a reference compound. The method also includes performing molar concentration-based detection on the separated first sample to determine a molar-based peak area for the reference compound. The method includes performing mass concentration-based detection on the separated first sample to determine a mass-based peak area for the reference compound. The method also includes performing liquid chromatographic separation of a second sample including one or more additional compounds. The method includes performing molar concentration-based detection on the separated second sample to determine a molar-based peak area for each of the one or more additional compounds. The method also includes performing mass-based detection on the separated second sample to determine a mass-based peak area for each of the one or more additional compounds. The method includes determining a relative response factor (RRF) for each of the one or more additional compounds based on the ratio of the molar-based peak area for the additional compound to the logarithm of the mass-based peak area for the additional compound and the ratio of the molar-based peak area for the reference compound to the logarithm of the mass-based peak area for the reference compound.

In another aspect, a method for determining relative concentrations of a reference compound and one or more additional compounds in a test sample includes determining relative response factors for the one or more additional compounds in accordance with the methods described herein. The method also includes performing liquid chromatographic separation of the test sample. The method includes performing molar concentration-based detection on the separated test sample to determine a molar-based peak area for the reference compound and for each of the one or more additional compounds. The method also includes applying the relative response factor for an additional compound to the molar-based peak area for the additional compound to obtain a corrected molar-based peak area for each of the one or more additional compounds in the test sample. The method includes determining the relative concentrations of the reference compound and the one or more additional compounds in the test sample based on the molar-based peak area of the reference compound and on the corrected molar-based peak area for each additional compound.

In another aspect, a method for determining concentrations of a reference compound and one or more additional compounds in a test sample includes determining relative response factors for the one or more additional compounds in accordance with the methods described herein. The method includes performing liquid chromatographic separation of the test sample. The method also includes performing molar concentration-based detection on the separated test sample to determine a molar-based peak area for the reference compound and for each of the one or more additional compounds. The method includes applying the relative response factor for an additional compound to the molar-based peak area for the additional compound to obtain a corrected molar-based peak area for each additional compound in the test sample. The methods includes determining the relative concentrations of the reference compound and the one or more additional compounds in the test sample based on the molar-based peak area of the reference compound and the corrected molar-based peak area for each additional compound. The method also includes performing liquid chromatographic separation of a reference sample including a known concentration of the reference compound. The method includes performing molar concentration-based detection on the reference sample to determine a molar-based peak area for the reference compound in the reference sample. The method also includes comparing the molar-based peak area of the reference compound in the reference sample to the molar-based peak area of reference compound in the test sample to obtain concentrations of the reference compound and the one or more additional compounds in the test sample from the determined relative concentrations of the reference compound and one or more additional compounds in the test sample.

In another aspect, a method of performing mass balance for a degraded sample including an active pharmaceutical ingredient (API) and one or more impurities includes determining relative response factors for the one or more impurities in accordance with the methods described herein with the reference compound being the API and the one or more additional compounds being the one or more impurities. The method also includes performing liquid chromatographic separation of an initial sample not subjected to degrading conditions. The method includes performing molar concentration-based detection on the separated initial sample to determine a molar-based peak area for the API and for each of the one or more impurities in the initial sample. The method includes applying the relative response factor for each of the one or more impurities to the molar-based peak area for the impurity to obtain a corrected molar-based peak area for each impurity in the initial sample. The method also includes performing liquid chromatographic separation of a degraded test sample, the degraded test sample being a test sample including the API that was previously subjected to degrading conditions. The method includes performing molar concentration-based detection on the separated degraded test sample to determine a molar-based peak area for the API and for each of the one or more impurities. The method also includes applying the relative response factor for an impurity to the molar-based peak area for the impurity to obtain a corrected molar-based peak area for each of the one or more impurities in the degraded test sample. The method includes comparing the sum of the corrected molar-based peak areas of the one or more impurities and the molar-based peak area of the API for the degraded sample with the sum of the corrected molar-based peak areas the one or more impurities and the molar-based peak area of the API for the initial sample to obtain a percentage recovery.

In another aspect, a method for determining relative concentrations of an active pharmaceutical ingredient (API) and one or more impurities in a test sample includes determining relative response factors for the one or more related impurities using in accordance with methods described herein with the reference compound being the API, the one or more additional compounds being the one or more impurities, the molar concentration-based detection being absorbance-based detection, and the mass concentration-based detection being evaporative light scattering detection (ELSD). The method also includes performing liquid chromatographic separation of the test sample. The method includes performing absorbance detection on the separated test sample to determine an absorbance peak area for the API and for each of the one or more related impurities. The method also includes applying the relative response factor for an impurity to the absorbance peak area for the impurity to obtain a corrected absorbance peak area for each of the one or more impurities in the test sample. The method includes determining the relative concentrations of the API and the one or more impurities in the test sample based on the absorbance peak of the API and on the corrected absorbance peak area for each impurity.

In another aspect, a method for determining concentrations of an active pharmaceutical ingredient (API) and one or more related impurities in a test sample includes determining relative response factors for the one or more related impurities in accordance with embodiments described herein with the reference compound being the API, the one or more additional compounds being the one or more impurities, the molar concentration-based detection being absorbance-based detection, and the mass concentration-based detection being evaporative light scattering detection (ELSD). The method also includes performing liquid chromatographic separation of the test sample. The method includes performing absorbance detection on the separated test sample to determine an absorbance peak area for the API and for each of the one or more related impurities. The method includes applying the relative response factor for an impurity to the absorbance peak area for the impurity to obtain a corrected absorbance peak area for each of the one or more impurities in the test sample. The method includes performing liquid chromatographic separation of a reference sample including a known concentration of the API. The method also includes performing absorbance detection on the reference sample to determine an absorbance peak area for the API in the reference sample. The method includes comparing the absorbance peak area of the API in the reference sample to the absorbance peak area of API in the test sample to obtain concentrations of the API and the one or more related impurities in the test sample from the determined relative concentrations of the API and one or more related impurities in the test sample.

In another aspect, a non-transitory computer-readable medium storing computer executable instructions for determining relative response factors includes instructions for determining a molar-based peak area for a reference compound and for each of one or more additional compounds from molar concentration-based detection of a chromatographically separated sample. The instructions include instructions for determining a mass-based peak area for the reference compound and for each of the one or more additional compounds from mass concentration-based detection of the chromatographically separated sample. The instructions also includes instructions for determining a relative response factor (RRF) for each of the one or more additional compounds, the relative response factor for an additional compound based on the ratio of the molar-based peak area for the additional compound to the logarithm of the mass-based peak area for the additional compound and the ratio of the molar-based peak area for the reference compound to the logarithm of the mass-based peak area for the reference compound.

In another aspect, a non-transitory computer-readable medium storing computer executable instructions for determining relative response factors includes instructions for determining a molar-based peak area for a reference compound from molar concentration-based detection of a chromatographically separated first sample. The instructions include instructions for determining a mass-based peak area for the reference compound from mass concentration-based detection of the chromatographically separated first sample. The instructions include instructions for determining a molar-based peak area for each of the one or more additional compounds from molar concentration-based detection of a chromatographically separated second sample. The instructions include instructions for determining a mass-based peak area for each of the one or more additional compounds from mass concentration-based detection of the chromatographically separated second sample. The instructions also include instructions for determining a relative response factor (RRF) for each of the one or more additional compounds, the relative response factor for an additional compound based on the ratio of the molar-based peak area for the additional compound to the logarithm of the mass-based peak area for the additional compound and the ratio of the molar-based peak area for the reference compound to the logarithm of the mass-based peak area for the reference compound.

In another aspect, a system includes a liquid chromatography column configured to perform liquid chromatographic separation of a sample including a reference compound and one or more additional compounds, a molar concentration-based detector, and a mass concentration-based detector. The system also includes a molar concentration-based detection module executed by one or more processors in a processing device and configured to perform molar concentration-based detection on the separated sample, using the molar concentration-based detector, to determine a molar-based peak area for the reference compound and for each of the one or more additional compounds. The system includes a mass concentration-based detection module executed by the one or more processors and configured to perform mass concentration-based detection on the separated sample, using the mass concentration-based detector, to determine a mass-based peak area for the reference compound and for each of the one or more additional compounds. The system includes a relative response factor module executed by the one or more processors. The relative response factor module is configured to: compute a first ratio of the molar-based peak area for the additional compound to a logarithm of the mass-based peak area for the additional compound; compute a second ratio of the molar-based peak area for the reference compound to a logarithm of the mass-based peak area for the reference compound; and compute a relative response factor for each of the one or more additional compounds based on the first ratio and the second ratio.

In another aspect, a system includes a chromatography control module executed by one or more processors in a processing device and configured to control liquid chromatographic separation of a sample including a reference compound and one or more additional compounds using a liquid chromatography column. The system also includes a molar concentration-based detection module executed by the one or more processors and configured to control molar concentration-based detection on the separated sample using a molar concentration-based detector and configured to determine a molar-based peak area for the reference compound and for each of the one or more additional compounds. The system includes a mass concentration-based detection module executed by the one or more processors and configured to control mass concentration-based detection on the separated sample using a mass concentration-based detector and configured to determine a mass-based peak area for the reference compound and for each of the one or more additional compounds. The system also includes a relative response factor module executed by the one or more processors. The relative response factor module is configured to: compute a first ratio of the molar-based peak area for the additional compound to a logarithm of the mass-based peak area for the additional compound; compute a second ratio of the molar-based peak area for the reference compound to a logarithm of the mass-based peak area for the reference compound; and compute a relative response factor for each of the one or more additional compounds based on the first ratio and the second ratio.

In some embodiments, the system also includes a mass balance module configured to determine a mass balance in the sample based on the molar-based peak areas in the sample for the reference compound and for each of the one or more additional compounds, and the relative response factors for each of the one or more additional compounds.

Embodiments can include one or more of the following features.

In some embodiments, the relative response factor for each of the one or more additional compounds ($RRF_{add\_cpnd}$) is a function of the ratio of the molar-based peak area for the additional compound ($Molar\_Area_{add\_cpnd}$) to the logarithm of the mass-based peak area for the additional compound ($\log(Mass\_Area_{add\_cpnd})$) divided by the ratio of the molar-based peak area for the reference compound ($Molar\_Area_{ref\_cpnd}$) to the logarithm of the mass-based peak area for the reference compound ($\log(Mass\_Area_{ref\_cpnd})$). In some embodiments, the relative response factor for each of the one or more impurities is described by the following equation:

$$RRF_{add\_cpnd} \propto \frac{Molar\_Area_{add\_cpnd}}{\log(Mass\_Area_{add\_cpnd})} \Big/ \frac{Molar\_Area_{ref\_cmpd}}{\log(Mass\_Area_{ref\_cmpd})}.$$

In some embodiments, the molar concentration-based detection is absorption spectroscopy in the ultraviolet-visible spectral region.

In some embodiments, the mass concentration-based detection is evaporative light scattering detection (ELSD).

In some embodiments, the liquid chromatographic separation includes high performance liquid chromatography.

In some embodiments, the chromatographic separation includes ultra-high performance liquid chromatography (UHPLC).

In some embodiments, the reference compound is an active pharmaceutical ingredient (API) and the one or more additional compounds are one or more impurities.

In some embodiments, the chromatographic separation is isocratic.

BRIEF DESCRIPTION OF THE FIGURES

The drawings are intended to illustrate the teachings taught herein and are not intended to show relative sizes and dimensions, or to limit the scope of examples or embodiments. In the drawings, the same numbers are used throughout the drawings to reference like features and components of like function.

FIG. 5A is a graph of absorbance peaks for an API and impurities.

FIG. 5B is a graph of normalized absorbance peaks for an API and impurities.

FIG. 10 includes two partial screen shots illustrating RRF calculations in a software environment, in accordance with some embodiments.

FIG. 11 includes tables showing example mass balance calculations based on forced degradation data, in accordance with some embodiments.

DETAILED DESCRIPTION OF CERTAIN EMBODIMENTS

Figure 1:
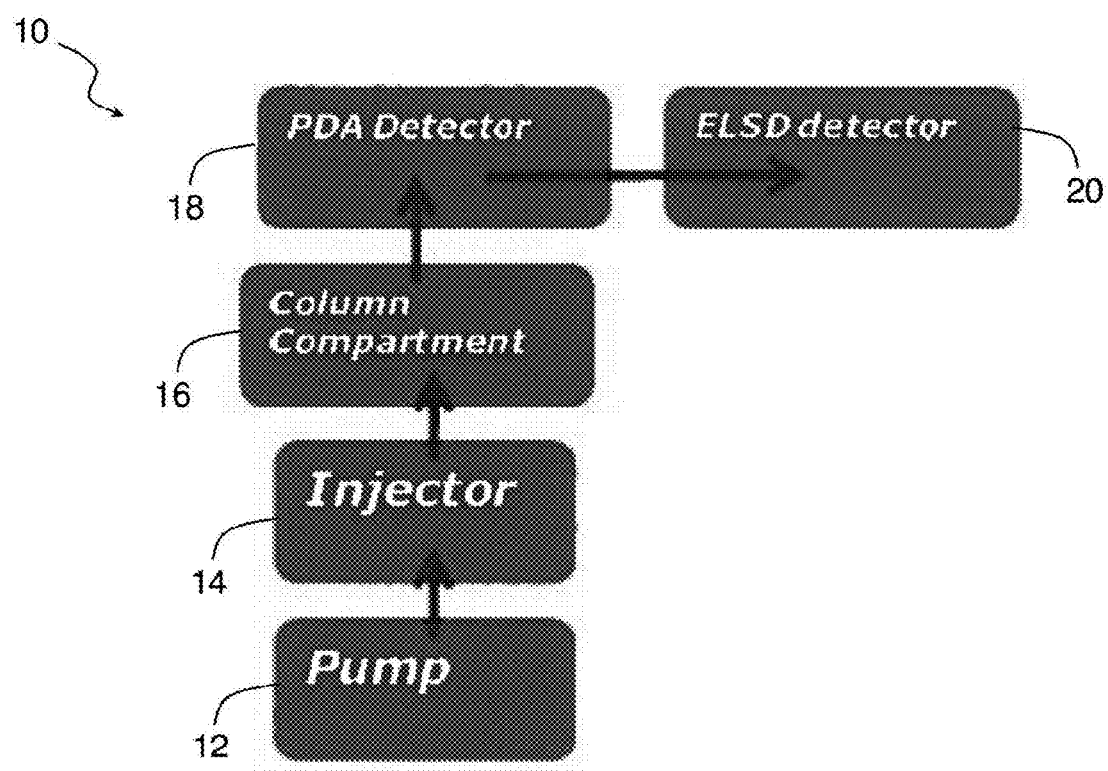
FIG. 1 schematically depicts a liquid chromatographic system including orthogonal detectors for practicing some embodiments described herein.

Some methods described herein employ both molar concentration-based detection and mass-concentration based detection of a chromatographically separated sample to determine relative response factors for a reference compound and one or more additional compounds. A combination of molar concentration-based detection and mass-concentration based detection may be described as orthogonal detection. Some methods described herein employing orthogonal detection for the determination of relative response factors avoid the need for isolation of the one or more additional compounds to generate calibration curves and avoid additional testing and experimentation required for generation of calibration curves.

As used herein, the term "reference compound" refers to a compound to which the one or more additional compounds are compared with respect to a detector response. In some embodiments, the reference compound may be a standard added to a sample. In some embodiments, the reference compound is an active pharmaceutical ingredient (API). In some embodiments, the reference could be a standard in a food or natural product sample (e.g., a single sugar food or catechin in the analysis of tea leaves).

In forced degradation studies, a drug product or drug substance including an API is subjected to various types of degradation conditions including acid hydrolysis, base hydrolysis, oxidation, or thermal degradation conditions. The table below lists examples of various degradation conditions.

| Degradation Type | Samples | Conditions |
|---|---|---|
| Acid Hydrolysis | 0.1 M HCl | 40° C. for 1, 3, 5, 7 days |
| Base Hydrolysis | 0.1 M NaOH | 40° C. for 1, 3, 5 7 days |
| Oxidation | 3% H$_2$O$_2$ | 25° C. for 1, 3, 5, 7 days |
| Thermal | Heating | |

Analysis in forced degradation studies incorporates mass balance. In mass balance, the total amounts of the API and all reactants are measured before degradation and after degradation to see how closely the assay values and levels of degradations add up to 100% of the initial value. During mass balance, impurities, specifically degradation products, must be summarized and measured relative to the API. Specifically, if the degradation product is at a level greater than a specified reporting threshold (e.g., a reporting threshold of 0.05%-0.1%) the degradation product must be identified or qualified. Among the critical factors impacting the mass balance measurement are co-elution, failure to detect impurities, poor recovery of the impurity or the parent, and response factor differences between the API and the impurities.

Impurities can be measured by comparing the analytical response of the impurities to that of a reference standard or a drug substance; however, the analytical response of the detector or analysis system to the impurity may be different than the analytical response of the detector or analysis system to the reference standard or the API. Accordingly, relative response factors and correction factors are used to address this difference in analysis response to the impurity and to the reference standard or the API. The ICH Impurity Testing Guidelines specifies that a relative response factor (RRF) greater than 1.2 or less than 0.8 generally should be applied in mass balance calculations. However, for accurate and detailed mass balance calculations, it may be desirable to also apply RRFs falling within the range of 1.2 to 0.8.

Some detection techniques are proportional to the molar concentration of a compound in a sample. Examples of such molar concentration-based techniques include ultraviolet-visible (UV-Vis) absorbance, chemiluminescent nitrogen detectors (CNLD), radiochemical detection, nuclear magnetic resonance (NMR), and mass spectrometry (MS). Other techniques have responses best approximated by the mass concentration of a compound in a sample. Examples of mass concentration-based detectors include evaporative light scattering detectors (ELSD) and charged aerosol detectors (CAD).

Calculations of the absolute mass balance deficit (AMBD) may be made using moles or grams. Employing a molar concentration-based technique to track moles instead of grams in mass balance calculations makes it possible to track degradation routes without having to measure all reactive species and degradation products.

When detecting a compound (e.g., an API or an impurity) in a sample, a response factor (RF) is the detector response divided by the concentration of the compound in the sample, which corresponds to the slope for the compound in a conventional calibration curve and may be described by the following equation.

$$RF_{compound} = \frac{\text{Peak } Area_{compound}}{Concentration_{compound}} = \text{Calibration Curve } Slope_{compound} \quad (1)$$

Conventionally, an RRF for a compound, is defined as the RF for the compound (e.g., an impurity) divided by the RF for the reference compound (e.g., the API or a standard), which corresponds to the calibration curve slope for the compound divided by the calibration curve slope for the reference compound as shown in the following equation.

$$RRF\_conventional_{compound} = \frac{RF_{compound}}{RF_{reference\ compound}} = \frac{Slope_{compound}}{Slope_{reference\ compound}} \quad (2)$$

Such an analysis above requires the use of multiple calibration samples with known concentrations of the reference compound and any additional compounds for which RRFs are needed. These calibration samples are required for generation of the calibration curves to determine the required slopes. The calibration curve method for determination of RRFs requires testing of multiple sample and assumes that samples with known concentrations of the additional compounds are available.

Methods described herein employ molar-based and mass-based detection techniques to determine RRFs without requiring generation of conventional calibration curves. Some methods described herein enable determination of RRFs based on testing of a single sample. Further, methods described herein do not require multiple samples with different known concentrations of a reference compound and of additional compounds to determine RRFs for the additional compounds.

In some embodiments, a method of determining RRFs includes performing liquid chromatographic separation of a sample including a reference compound and one or more additional compounds. As used herein, the term additional compound refers to any compound that is not the reference compound. In some embodiments the liquid chromatographic separation is high performance liquid chromatography. In some embodiments the liquid chromatographic separation is ultra-high performance liquid chromatography.

Molar concentration-based detection (e.g., UV-Vis absorbance) is performed on the separated sample to determine a molar-based peak area for the reference compound and for each of the one or more additional compounds. Mass concentration-based detection (e.g., ELSD) is also performed on the separated sample to determine a mass-based peak area for the reference compound and for each of the one or more additional compounds.

An RRF is determined for each of the one or more additional compounds based on the ratio of the molar-based peak area for the additional compound to the logarithm of the mass-based peak area for the additional compound and the ratio of the molar-based peak area for the reference compound to the logarithm of the mass-based peak area for the reference compound.

In some embodiments relative response factor for each of the one or more additional compounds ($RRF_{add\_cpnd}$) is a function of the ratio of the molar-based peak area for the additional compound ($Molar\_Area_{add\_cpnd}$) to the logarithm of the mass-based peak area for the additional compound ($\log(Mass\_Area_{add\_cpnd})$) divided by the ratio of the molar-based peak area for the reference compound ($Molar\_Area_{ref\_cpnd}$) to the logarithm of the mass-based peak area for the reference compound ($\log(Mass\_Area_{ref\_cpnd})$).

In some embodiments, the relative response factor for an additional compound is described by the following equation:

$$RRF_{add\_cpnd} \propto \frac{Molar\_Area_{add\_cpnd}}{\log(Mass\_Area_{add\_cpnd})} \bigg/ \frac{Molar\_Area_{ref\_cmpd}}{\log(Mass\_Area_{ref\_cmpd})} \quad (3)$$

In some embodiments, the relative response factor for an additional compound is described by the following equation:

$$RRF_{add\_cpnd} = \frac{Molar\_Area_{add\_cpnd}}{\log(Mass\_Area_{add\_cpnd})} \bigg/ \frac{Molar\_Area_{ref\_cmpd}}{\log(Mass\_Area_{ref\_cmpd})} \quad (4)$$

Equations 3 and 4 above for RRF assume that a correction factor that is multiplied to a peak area to generate a corrected peak area is equal to 1/RFF.

Some define the RRF itself as the correction factor that is multiplied to a peak area to generate a corrected peak area. With this alternative definition of the RRF, the RRF would instead be proportional to the ratio of the molar-based peak area for the reference compound ($Molar\_Area_{ref\_cpnd}$) to the logarithm of the mass-based peak area for the reference compound ($\log(Mass\_Area_{ref\_cpnd})$) divided by the ratio of the molar-based peak area for the additional compound ($Molar\_Area_{add\_cpnd}$) to the logarithm of the mass-based peak area for the additional compound ($\log(Mass\_Area_{add\_cpnd})$).

In the embodiment described above for determining the RRF, the molar-based peak area and the mass-based peak area for the reference compound are determined based on the same sample as that used to determine the molar-based peak areas and the mass-based peak areas for the one or more additional compounds. In some other embodiments, multiple different samples may be employed. For example, in another method, liquid chromatographic separation is performed to separate a first sample including a reference compound. Molar concentration-based detection is performed on the separated first sample to determine a molar-based peak area for the reference compound. Mass concentration-based detection is performed on the separated first sample to determine a mass-based peak area for the reference compound. Liquid chromatographic separation is performed to separate a second sample including one or more additional compounds. Molar concentration-based detection is performed on the separated second sample to determine a molar-based peak area for each of the one or more additional compounds. Mass concentration-based detection is performed on the separated second sample to determine a mass-based peak area for each of the one or more additional compounds.

Embodiments also include methods for determining relative concentrations of a reference compound and one or more additional compounds. RRFs are determined for the one or more additional compounds using one of the methods described herein. Liquid chromatographic separation is performed on the test sample. Molar concentration-based detection is performed on the separated test sample to determine a molar-based peak area for the reference compound and for each of the one or more additional compounds. For each additional compound, the relative response factor for the additional compound is applied to the molar-based peak area for the additional compound to obtain a corrected molar-mass based peak area for each additional compound in the test sample.

For RRFs defined according to equations 3 or 4 above, a corrected molar-mass based peak area for an additional compound would be obtained by multiplying the molar-based peak area measured for the additional compound in the test sample by a correction factor of $1/RRF_{add\_cpnd}$. For the alternative definition of RRFs, in which the RRF is defined as proportional to the ratio of the molar-based peak area for the reference compound to the logarithm of the mass-based peak area for the reference compound divided by the ratio of the molar-based peak area for the additional compound to the logarithm of the mass-based peak area for the additional compound, a corrected molar-mass based peak area for an additional compound would be obtained by multiplying the molar-based peak area measured for the additional compound in the test sample by the RRF for the additional compound.

After the corrected molar-based peaks areas are determined for all of the additional compounds in the test sample, the molar-based peak area for the reference compound and the corrected molar-based peak areas for the additional compounds can be combined to determine the relative concentrations of the reference compound and the one or more additional compounds in the test sample. Specifically, the molar-based peak area for the reference compound and the corrected molar-based peak areas for the additional compounds would be added to obtain a total corrected molar-based peak area. The relative concentration of the reference compound in the test sample is the molar-based peak area for the reference compound divided by the total corrected molar-based peak area. The relative concentration of each additional compound in the test sample is the corrected molar-based peak area for the additional compound divided by the total corrected molar-based peak area.

In some embodiments, the method described above for determining relative concentrations of a reference compound and one or more additional compounds may be modified for use in determining concentrations of the reference compound and one or more additional compounds. Specifically, the method may further include performing liquid chromatographic separation of a reference sample including a known concentration of the reference compound and performing molar concentration-based detection on the reference sample to determine a molar-based peak area for the reference compound in the reference sample. Concentrations of the reference compound and the one or more additional compounds in the test sample can be determined by comparing the molar-based peak area of the reference compound in the reference sample to the known concentration of the reference compound in the reference sample and to the molar-based peak area of reference compound in the test sample.

In some embodiments, the reference compound is a API and the one or more additional compounds are one or more impurities. In some embodiments, the chromatographic separation is isocratic.

Some embodiments include a method of performing mass balance for a degraded sample including an API and one or more impurities. The method includes determining RRFs for the one or more impurities using methods described herein with the reference compound being the API and the one or more additional compounds being the one or more impurities. The method also includes performing liquid chromatographic separation of an initial sample not subjected to degrading conditions. Molar concentration-based detection is conducted on the separated initial sample to determine a molar-based peak area for the reference compound and for each of the one or more additional compounds in the initial sample. The RRF for each of the one or more additional compounds is applied to the molar-based peak area for the additional compound to obtain a corrected molar-based peak area for each additional compound in the initial sample. Liquid chromatographic separation is performed on a degraded test sample where the degraded test sample is a test sample including the API that was previously subjected to degrading conditions (e.g., acid hydrolysis, base hydrolysis, oxidation or thermal degradation conditions). Molar concentration-based detection is performed on the separated degraded test sample to determine a molar-based peak area for the API and for each of the one or more impurities. For each of the impurities, the relative response factor for the impurity is applied to the molar-based peak area for the impurity to obtain a corrected molar-based peak area for the impurity in the degraded test sample. The sum of the corrected molar-based peak areas of the one or more impurities and the molar-based peak area of the API for the degraded sample is compared with the sum of the corrected molar-based peak areas for the one or more impurities and the molar-based peak area of the API for the initial sample to obtain a percentage recovery.

In some embodiments, molar-based concentration detection is performed with a UV-Vis absorbance detector (e.g., a photodiode array (PDA) detector) and the mass-based concentration detection is performed with an ELSD detector. FIG. 1 schematically depicts a chromatographic analysis system 10 for performing some of the methods described herein. The system 10 includes a pump 12, an injector 14, which may also be described as a sample manager, a column compartment 16 including a chromatographic column, a PDA detector 18, and an ELSD detector 20. The pump 12 begins flow to the column in the column compartment 16. The injector 14 injects the sample and the separation occurs in the column. The PDA detector 18, a molar concentration-based detector, detects analytes based on extinction coefficients. The ELSD detector 20, a mass concentration-based detector, detects analytes based on particulate size.

Figure 2:
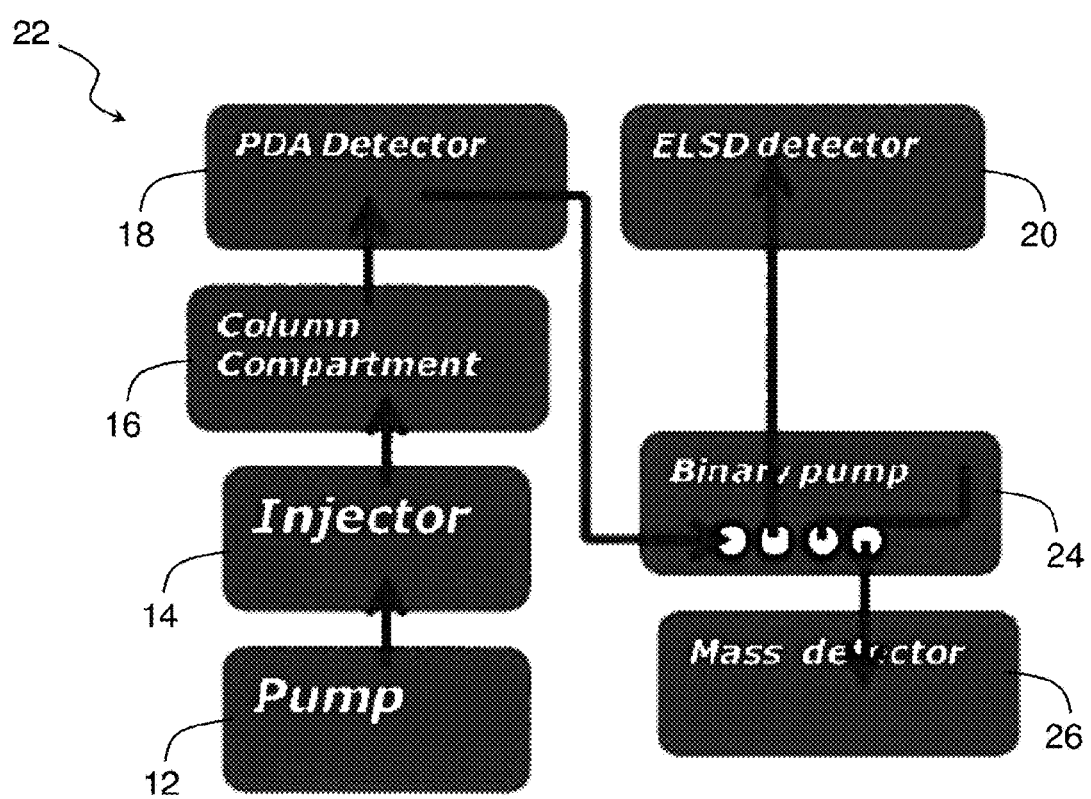
FIG. 2 schematically depicts another system liquid chromatographic system including orthogonal detectors for practicing some embodiments described herein.

FIG. 2 schematically depicts another chromatographic analysis system 22 for performing methods described herein. System 22 includes a pump 12, an injector 14, a column compartment 16 including chromatographic column, a PDA detector 18, and an ELSD detector 20. System 22 additionally includes an isocratic pump 24 that divides the separated sample between the ELSD detector 20 and a mass detector 26 with the use of a splitter. Because both the ELSD detector 20 and the mass detector 26 employ destructive measurement techniques, the isocratic pump 24 functions as a makeup flow pump.

Either or both of system 10 and system 22 may further include a chromatography data system (not shown). An example of such a chromatography data system is the EMPOWER 3 chromatography data software from Waters Technologies Corporation of Milford, Mass.

Some embodiments include a non-transitory computer-readable medium storing computer executable instructions for determining relative response factors in accordance with methods described herein. In some embodiments, the instructions including instructions for determining a molar-based peak area for a reference compound and for each of one or more additional compounds from molar concentration-based detection of a chromatographically separated sample. The instructions also include instructions for determining a mass-based peak area for the reference compound and for each of the one or more additional compounds from mass concentration-based detection of the chromatographically separated sample. The instructions further include instructions for determining an RRF for each of the one or more additional compounds with the relative response factor for an additional compound based on the ratio of the molar-based peak area for the additional compound to the logarithm of the mass-based peak area for the additional compound and the ratio of the molar-based peak area for the reference compound to the logarithm of the mass-based peak area for the reference compound.

In some embodiments, the instructions including instructions for determining a molar-based peak area for a reference compound from molar concentration-based detection of a chromatographically separated first sample. Instructions for determining a mass-based peak area for the reference compound from mass concentration-based detection of the chromatographically separated first sample are also included. Instructions for determining a molar-based peak area for each of the one or more additional compounds from molar concentration-based detection of a chromatographically separated second sample are included. Instructions for determining a mass-based peak area for each of the one or more additional compounds from mass concentration-based detection of the chromatographically separated second sample are also included. Instructions for determining a relative response factor (RRF) for each of the one or more additional compounds are included, where the relative response factor for an additional compound based on the ratio of the molar-based peak area for the additional compound to the logarithm of the mass-based peak area for the additional compound and the ratio of the molar-based peak area for the reference compound to the logarithm of the mass-based peak area for the reference compound.

In some embodiments, the computer executable instructions may be instructions executable within chromatography data software executing on a computing device or computing system associated with a chromatography analysis system. In some embodiments, the computer executable instructions may be instructions executable within chromatography data software executing on a computing device or computing system not associated with a chromatography analysis system. For example, the instructions may be implemented, at least in part, as a template project within the EMPOWER 3 chromatography data software environment. As another example, the instructions may be implemented, at least in part, as one or more custom fields within the EMPOWER 3 chromatography data software environment. Examples of custom fields that may be employed in some embodiments include, but are not limited to: a field that calculates the log of the area of a peak; a field that calculates the ratio of the peak area from a molar-based detection channel (e.g., UV-vis) for an impurity to the log of the peak area from a mass-based detection channel (e.g., ELSD) for the impurity divided by the ratio of the peak area from the molar-based detection channel (e.g., UV-vis) for the reference (e.g., API) to the log of the peak area from a mass-based detection channel (e.g., ELSD) for the reference; a field that calculates the sum total area of the peaks in a sample chromatogram to the sum total area of peaks in a reference chromatogram multiplied by 100; a field that divides the area of any known peak by the relative response factor to obtain corrected peak areas; and a field that compares the sum total corrected area of the peaks in a sample chromatogram with the sum total corrected area of the peaks in a reference chromatogram multiplied by 100.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a laboratory environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice.

Figure 22:
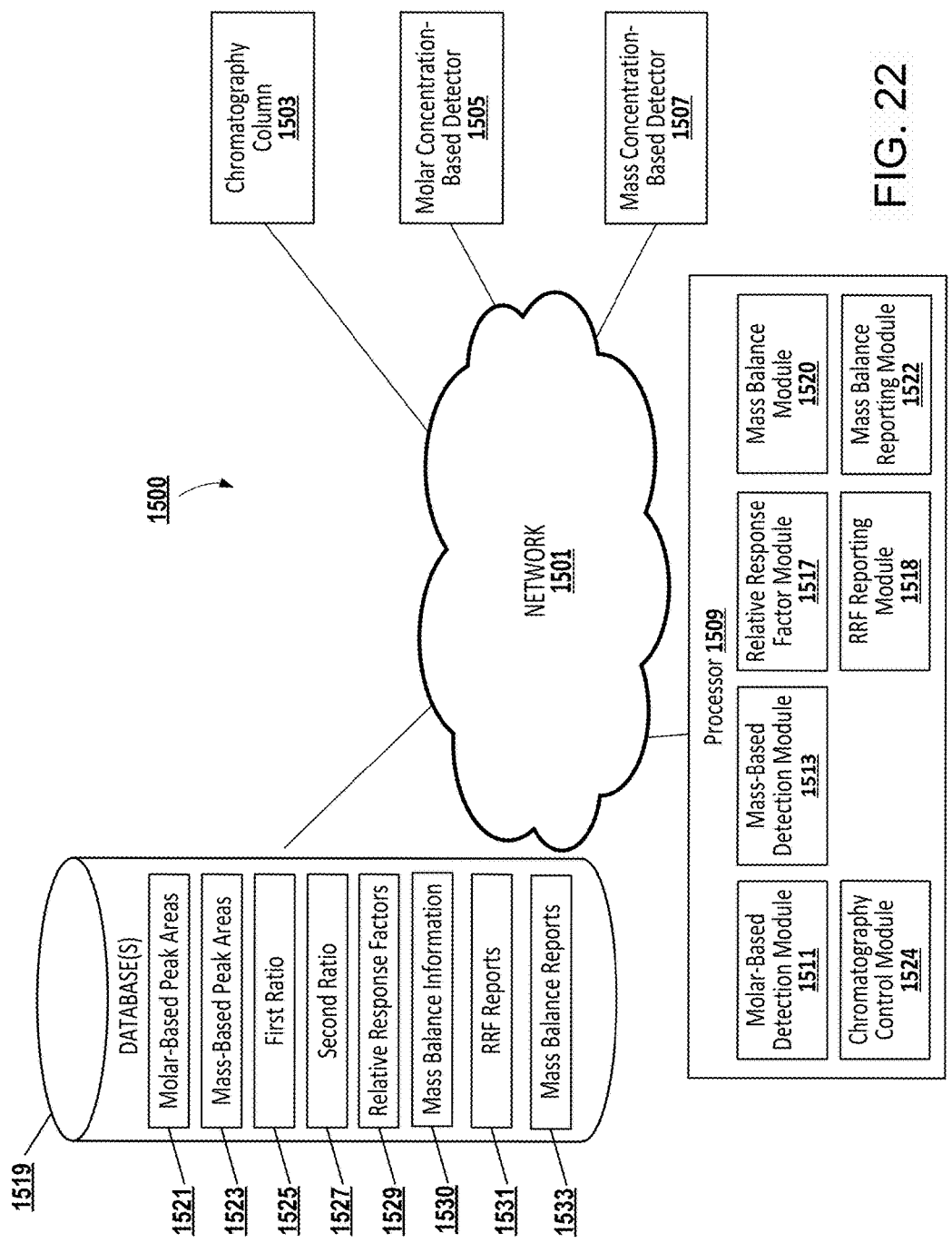
FIG. 22 is a diagram of an exemplary system suitable for an implementation of an exemplary embodiment of the present disclosure.

FIG. 22 illustrates an exemplary block diagram depicting a system 1500 suitable for implementation of some exemplary embodiments of the present disclosure. In exemplary embodiments, the system for determining relative response factors 1500 can include a liquid chromatography column 1503 for performing liquid chromatographic separation of a sample including a reference compound and one or more additional compounds. The system 1500 can also include a network 1501, a molar concentration-based detector 1505, and a mass concentration-based detector 1507. The system 1500 can also include, in some embodiments, one or more processors 1509 or servers configured to execute computer-readable instructions and/or software, such as a chromatography control module 1524, a molar concentration-based detection module 1511, a mass concentration-based detection module 1513, a relative response factor module 1517, an RRF reporting module 1518, a mass balance module 1520, and a mass balance reporting module. It will be appreciated that the module functionality may be combined or divided as a greater or lesser number of modules than illustrated, and that the same processor or server could host one or more modules. In one example embodiment, the system 1500 can determine a molar-based peak area for the reference compound and for each of the additional compounds by executing the molar concentration-based detection module 1511 in order to perform a molar concentration-based detection on the separated sample using the molar concentration-based detector 1505. The system 1500 can also determine a mass-based peak area for the reference compound and for each of the additional compounds by executing the mass concentration-based detection module 1513 in order to perform a mass concentration-based detection on the separated sample using the mass concentration-based detector 1507. The system 1500 can also execute the relative response factor module 1517 to determine a relative response factor for each of the additional compounds. In one example embodiment, the relative response factor module 1517 computes a first ratio of the molar-based peak area for the additional compound to the logarithm of the mass-based peak area for the additional compound. The relative response factor module can also compute a second ratio of the molar-based peak area for the reference compound to the logarithm of the mass-based peak area for the reference compound. Once the first ratio and the second ratio have been computed, the relative response factor module 1517 can compute the relative response factor for each of the additional compounds based, at least in part, on the first ratio and the second ratio. In some embodiments, the mass balance module 1520 can use output from the molar-based detection module 1511 and the relative response factor module 1517 to perform a mass balance for a sample.

The communication network 1501 may include, but is not limited to, the Internet, an intranet, a LAN (Local Area Network), a WAN (Wide Area Network), a MAN (Metropolitan Area Network), a wireless network, an optical network, and the like. In some embodiments, chromatography column 1503, molar concentration-based detector 1505, mass concentration-based detector 1507, processor 1509, and the database 1519 can transmit instructions to each other over the communication network 1501

In some embodiments, the system for determining relative response factors 1500 can also include one or more databases 1519 for storing any suitable information required to implement exemplary embodiments of the methods and systems taught herein. For example, a database 1519 can store the molar-based peak areas 1521 for the reference compound and for each of the additional compounds, as well as the mass-based peak areas 1523 for the reference compound and for each of the additional compounds. The database 1519 can also store the first ratio 1525 and the second ratio 1527 computed by the relative response factor module 1517, as well as the relative response factors 1529 for each of the additional components. The database 1519 can also store information used for the mass balance and mass balance results 1530.

The system for determining relative response factors 1500 can also include a relative response factor reporting module 11518, in some embodiments. The relative response factor reporting module 1518 can be configured to generate a report including various metrics calculated by the system 1500. For example, the relative response factor reporting module 1518 can generate a report including the molar-based peak area for the reference compound and for each of the additional compounds, the mass-based peak area for the reference compound and for each of the additional compounds, the first ratio of the molar-based peak area for the additional compound to the logarithm of the mass-based peak area for the additional compound, the second ratio of the molar-based peak area for the reference compound to the logarithm of the mass-based peak area for the reference compound, and the relative response factor for each of the additional compounds. In some embodiments, the relative response factor reporting module 1518 can be configured to store relative response factor reports 1531 in the database 1519 or output the relative response factor reports 1531 by transmitting a copy of the reports to a user. As will be appreciated, the relative response factor reporting module 1518 can be executed by the same or a different processor as the molar concentration-based detection module 1511, the mass concentration-based detection module 1513, and the relative response factor module 1517.

Figure 23:
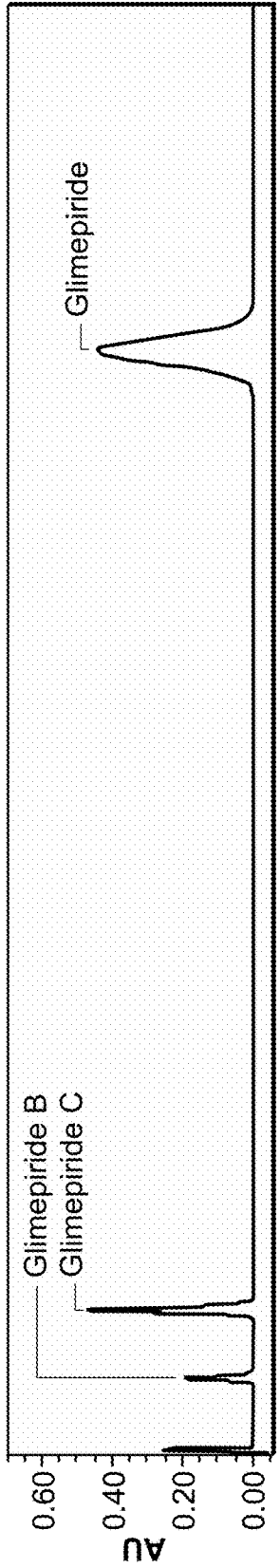
FIG. 23 is an image of a display of a summary portion of an example mass balance report, in accordance with some embodiments.
Figure 23:
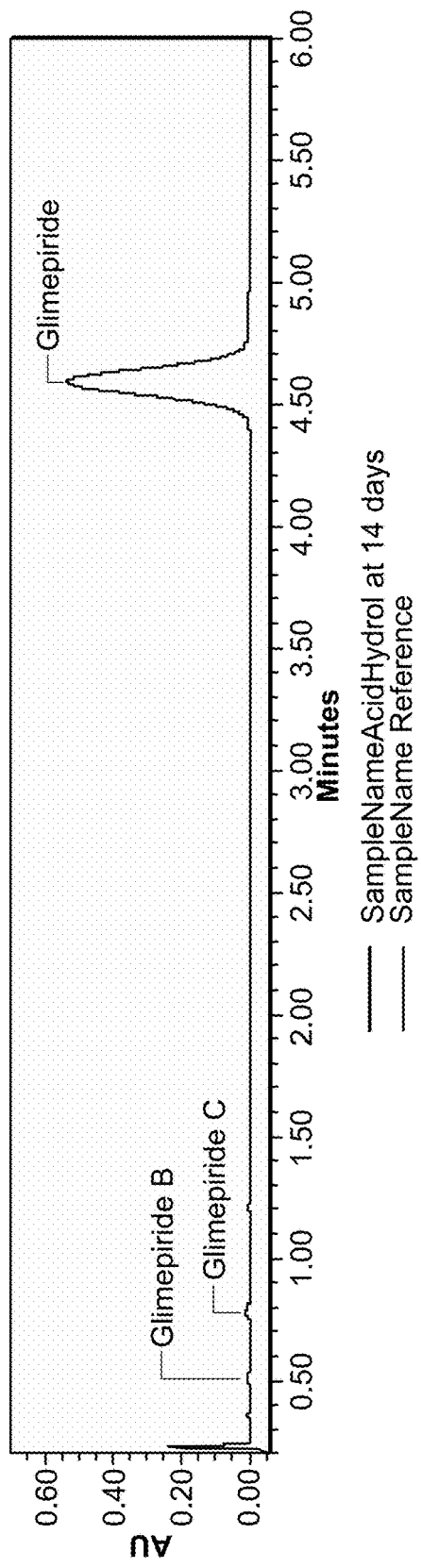

In some embodiments, the system also includes the mass balance module 1520 that performs mass balance calculations based on data from an undegraded reference sample, data obtained from a degraded sample, and calculated relative response factors. In some embodiments, the system also includes a mass balance reporting module 1522 configured to store a mass balance report 1533 in the database 1519, display a mass balance report 1533 or transmit a mass balance report 1533 to a user. As will be appreciated, the mass balance reporting module 1522 can be executed by the same or a different processor as the molar concentration-based detection module 1511, the mass concentration-based detection module 1513, the relative response factor module 1517, and the relative response factor reporting module 1518. FIG. 23 includes an image of a display of a summary portion of an example mass balance report.

In one exemplary embodiment, a user can interact with the system for determining relative response factors 1500 in order to create a customized system project. In one such embodiment, the customized system project can include computer-executable instructions that can prompt the various system modules 1511, 1513, 1517, 1518 to perform one or more of the functions described above. For example, a user can generate a customized system project that instructs the system 1500 to perform a liquid chromatographic separation of a particular sample. After separation of the sample into a reference compound and one or more additional compounds and detection of the separated sample, the customized system project can instruct the molar concentration-based detection module 1511 to compute the molar-based peak area for the reference compound and for each of the additional compounds. Similarly, the customized system project can instruct the mass concentration-based detection module 1513 to compute the mass-based peak area for the reference compound and for each of the additional compounds. The customized system project can also prompt the relative response factor module 1517 to compute the relative response factors for each of the additional compounds, as described above. In some embodiments, the customized system project can also prompt the relative response factor reporting module 1518 and/or the mass balance reporting module 15200 to generate and output a report, as described above.

The mass balance module 1520 and the mass balance reporting module 1522 may be particularly useful when performing stability analysis to satisfy regulatory requirements as they provide reliable and predictable tracking of data obtained and analysis performed for the mass balance.

The present invention is next described by means of the following examples. However, the use of these and other examples anywhere in the specification is illustrative only, and in no way limits the scope and meaning of the invention or of any exemplified form. The invention is not limited to any particular preferred embodiments described herein. Many modifications and variations of the invention may be apparent to those skilled in the art and can be made without departing from its spirit and scope. The contents of all references, patents and published patent applications cited throughout this application, including the figures, are incorporated herein by reference.

Example 1

The inventors conducted a determination of relative response factors (RRFs) and mass balance for degradation of a drug substance, specifically glimepiride, using both a conventional method for determining RRFs requiring the generation of calibration curves using samples with known concentrations of the compounds of interest, and using a method for determining RRF according to embodiments described herein.

The inventors conducted an acid hydrolysis of glimepiride, which has the chemical formula ($C_{24}H_{34}N_4O_5S$) 1-[[4-[2[(3-ethyl-4-methyl-2-oxo-3pyrroline-1-carboxamido)ethyl]phenyl]-sulphony]-3-trans-(4-methylcyclohexyl) urea], a molecular weight of 490.62, and a pKa value of 4.32. The chemical structure of glimepiride appears below.

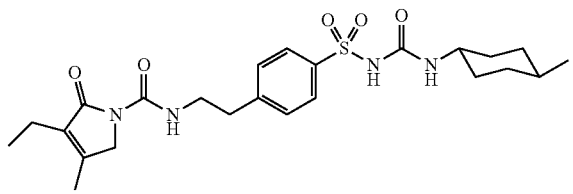 [SMILES: CCC1=C(C)CN(C(=O)NCCc2ccc(S(=O)(=O)NC(=O)NC3CCC(C)CC3)cc2)C1=O]

Glimepiride is a sulfonylurea antidiabetic medicine with a maximum daily dose of 8 mg. It is an acidic compound that is soluble in methanol at 0.5 mg/mL. The glimepiride degraded into two related compounds labeled compound B (3-Ethyl-4-methyl-2-oxo-N-(4-sulfamoylphenethyl)-2,5-dihydro-1H-pyrrole-1-carboxamide), and compound C (methyl((4-(2-(3-ethyl-4-methyl-2-oxo-2,5-dihydro-1H-pyrrole-1-carboxamido)ethyl)phenyl)sulfonyl)carbamate). Samples of related compound B and related compound C were obtained for calibration samples for a conventional RRF analysis. The structures of related compound B and related compound C are shown below.

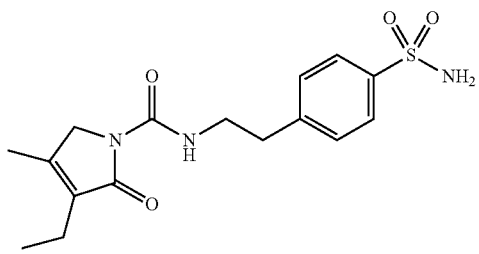

Glimepiride related compound B
MW 351.4

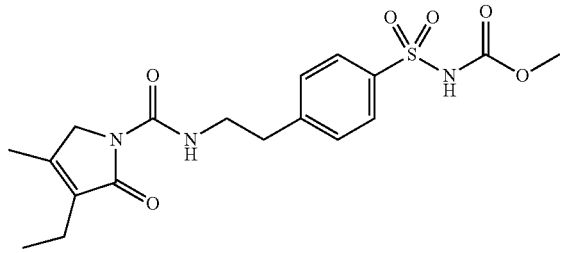

Glimepiride related compound C
MW 409.5

Experimental Apparatus and Conditions

The controls and the samples that underwent acid hydrolysis were subjected to the following conditions.

| Samples | Conditions |
| --- | --- |
| API Control | RT and 40° C. for 1, 3, 5, 7 days |
| Acid Control | RT and 40° C. for 1, 3, 5, 7 days |
| Acid Hydrolysis | RT and 40° C. for 1, 3, 5, 7 days |

Samples were analyzed using an ultra-high performance liquid chromatography system, specifically the ACUITY UPLC H-Class system from Waters Technologies Corporation. The system included photodiode array (PDA) and ELSD detectors, a quadrapole mass detector, specifically the Qda detector from Waters Technologies Corporation, and solvent and column managers. The PDA detector was used as a detector for UV-Vis absorbance. An ultra-high performance liquid chromatography column with 1.7 µm particle size and 2.1×50 mm column dimensions, specifically the ACUITY UPLC BEH C18 column from Waters Technologies Corporation, was used. The isocratic solvent manager was used with a flow rate of 0.3 mL/min and with 0.1% formic acid in methanol as a solvent. The following settings were used for the PDA and ELSD detectors.

| PDA | ELSD |
| --- | --- |
| Wavelength Range: 210-400 nm | Gas: 25 psi |
| Resolution: 3.6 nm | Nebulizer mode: cooling |
| Selected wavelengths: 228 and 254 nm, 4.8 nm resolution | Nebulizer temperature: 55° C. |
| Time constant: Normal | Gain: 350 |
| Sampling rate 20 pts/s | Data rate: 10 pps |

The mass detector was used with a mass range of 100-600, a cone voltage of 5 V, a sampling rate of 5, a capillary voltage of 1.4 kV. Single ion recording (SIR) was performed with the values in the table shown below.

SIR Parameters

| | Name | Mass (Da) | Polarity | Cone Voltage (V) |
| --- | --- | --- | --- | --- |
| 1 | Glimep + N | 513.60 | Positive | 10 |
| 2 | Glimep | 490.60 | Positive | 10 |
| 3 | Rel Cm B | 374.20 | Positive | 10 |
| 4 | Rel Cmp C | 432.20 | Positive | 10 |
| 5 | HMS | 114.00 | Positive | 10 |

Isocratic and gradients methods were developed for separation of impurities; however, the isocratic method was preferred as changing the solvent composition can affect the response and the size of droplets in ELSD. Mobile phase A was 0.1% (v/v) formic acid in water. Mobile phase B was 0.1% (v/v) formic acid in acetonitrile. The column temperature was 30° C. The injection volume was 2 µL. The flow rate was 0.8 mL/min. The isocratic tests included 60% mobile phase A and 40% mobile phase B. Conditions for the gradient tests are listed below. The system has a quaternary pump with four channels; however, only the A and B channels were used, which is why the C and D values are zero in the table below.

| Time (min) | % A | % B | % C | % D | Curve |
|---|---|---|---|---|---|
| Initial | 95.0 | 5.0 | 0.0 | 0.0 | Initial |
| 5.00 | 5.0 | 95.0 | 0.0 | 0.0 | 6 |
| 6.50 | 5.0 | 95.0 | 0.0 | 0.0 | 6 |
| 6.51 | 95.0 | 5.0 | 0.0 | 0.0 | 6 |

Calculation of RRFs Using Conventional Slopes of Calibration Curves

Figure 3:
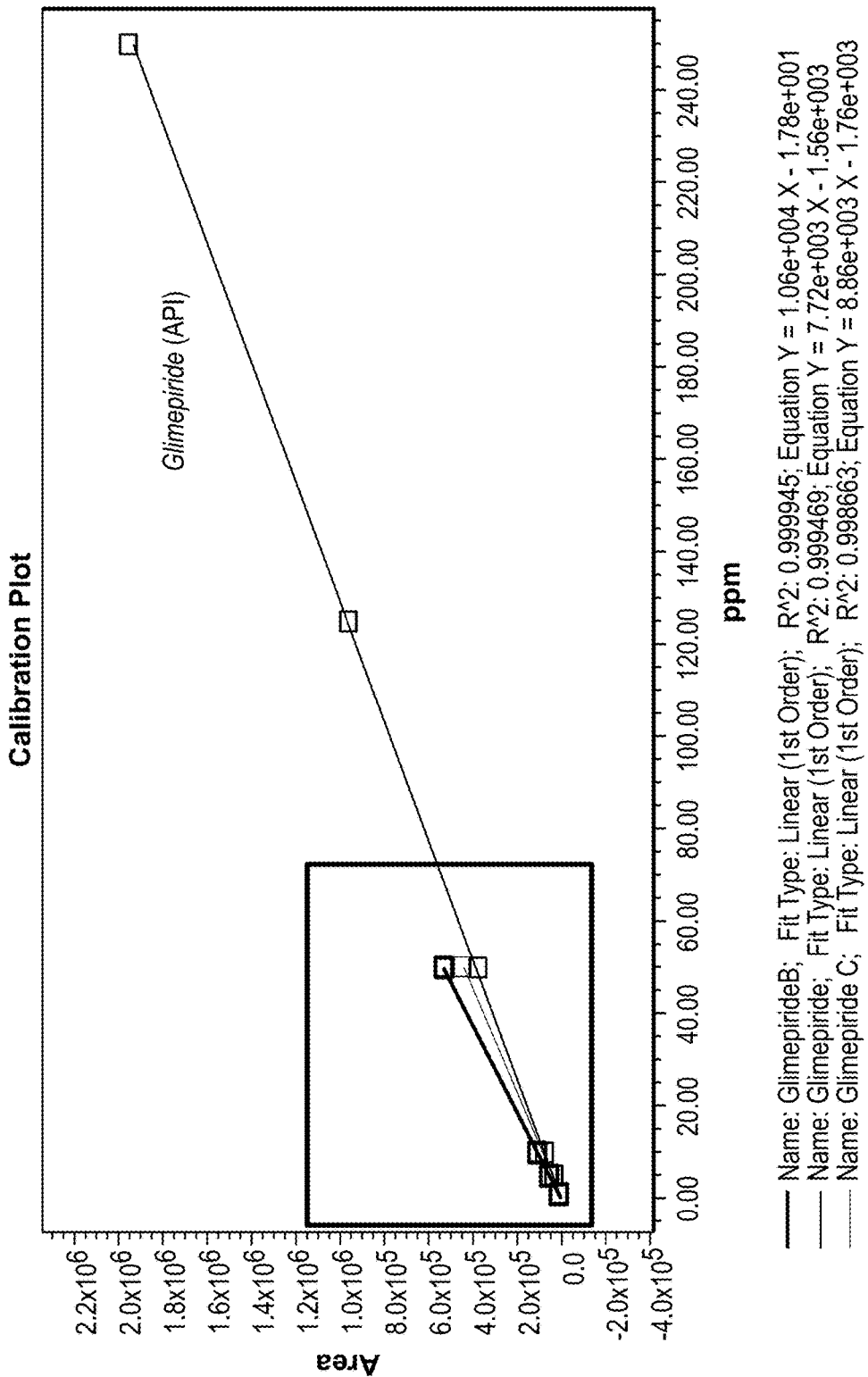
FIG. 3 is a graph of absorbance peak area versus concentration for analysis of multiple samples having different known concentrations of an API and impurities, which are used for conventional calibration curve determination of RRFs.
Figure 4:
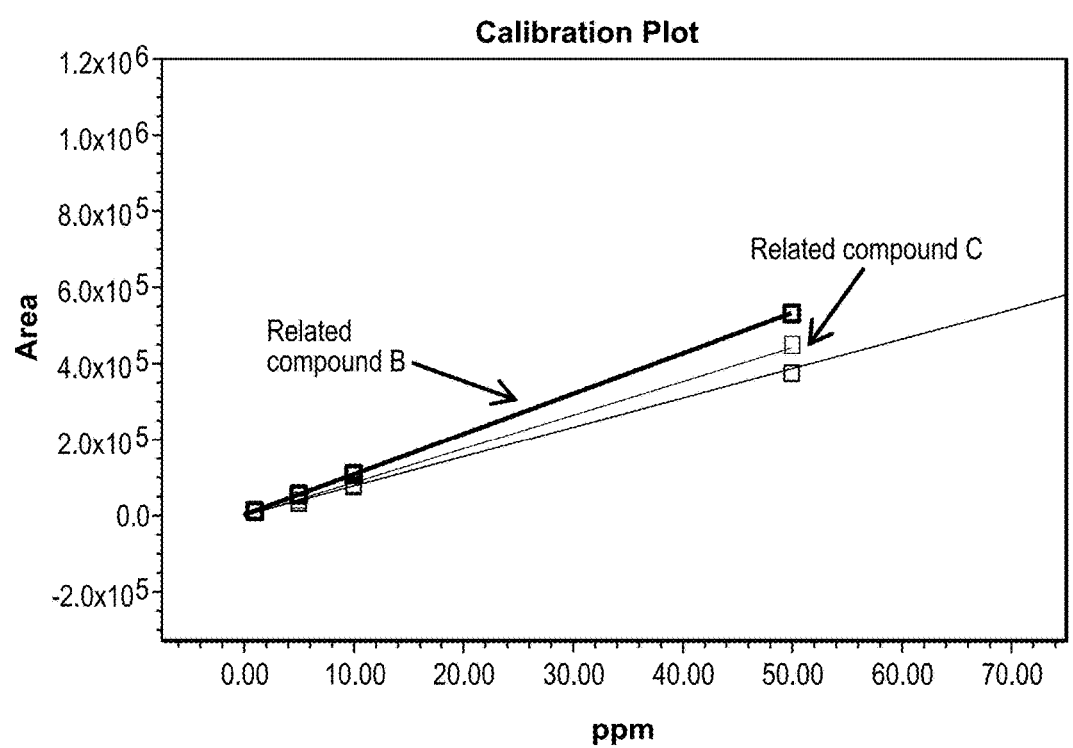
FIG. 4 is a detail of the graph of FIG. 3.

The inventors calculated RRFs using the conventional method involving measuring standards to determine the slopes of calibration curves as described below. Standards were acquired for the impurities (i.e., related compound B and related compound C) and for the API (i.e., glimepiride). Samples with various known concentrations of the impurities and the API were analyzed using the PDA detection system to generate calibration curves. Using the PDA, spectra of the API and the related impurities were compared to select a suitable wavelength for analysis. FIG. 3 shows graphs with calibration curves, specifically graphs of PDA peak area versus concentration for glimepiride, related compound B and related compound C. FIG. 4 is a detail of the graph of FIG. 3. As noted above, a response factor (RF) is the ratio of the detector response (e.g., peak area) of a compound (e.g., a standard compound, a reference compound, an API, or an impurity) to the concentration of the compound in the sample analyzed according to equation 1 above.

In the conventional method of determining RRF, the RRF for a compound is the RF of the compound divided by the RF of a reference compound, which for this example would be the RF of the impurity divided by the RF of the API. In terms of calibration curves, this would be the slope of the calibration curve for the impurity divided by the slope of the calibration curve for the API, which is represented by the following equation.

$$RRF\_conventional_{impurity} = \frac{[\text{Response of Impurity}]}{[\text{Response of API}]} = \frac{[\text{Slope of Impurity}]}{[\text{Slope of API}]} \quad (5)$$

FIG. 5A is a graph showing actual responses of the PDA to the API and impurities. FIG. 5B is a graph of normalized responses of the API and impurities at the wavelength of 228 nm.

The separation conditions and the wavelength selected altered the RRF determined for the impurities. The table below shows how the separation conditions being isocratic or gradient and the wavelength selected for absorbance detection affected the RRF factors determined using the conventional calibration curve method.

| Wavelength (nm) | Separation Conditions | RRF Rel Compound B | RRF Rel Compound C |
|---|---|---|---|
| 228 | Isocratic | 1.36 | 1.1 |
| 228 | Gradient | 1.24 | 1.06 |
| 254 | Isocratic | 1.24 | 1.08 |
| 254 | Gradient | 1.4 | 1.14 |

Example calculations for the isocratic method at 228 nm appear below:

$$RRF = \frac{[\text{Slope of Related Compound } B]}{[\text{Slope of Glimepride}]} = \frac{1.07e^{+004}}{7.86e^{+003}} = 1.36$$

$$RRF = \frac{[\text{Slope of Related Compound } C]}{[\text{Slope of Glimepride}]} = \frac{8.66e^{+003}}{7.86e^{+003}} = 1.12$$

The wavelength of 228 nm was selected for further analysis; however, the responses of the API and the impurities could have been evaluated at another single wavelength (e.g., 254 nm). For further analysis, the isocratic method was employed as changing the solvent composition could affect the response and the size of droplets in ELSD.

Calculation of RRF Using Molar-Based and Mass-Based Detection

Before describing example determinations of RRFs using molar-based and mass-based detection techniques in accordance with embodiments describe herein. An incorrect method of determining RRFs based on orthogonal detection techniques is addressed. When considering how to use orthogonal detection to determine RRFs without employing calibration curves, one may assume that an RRF calculated based on orthogonal detection would be the ratio of the molar-based peak area for a compound, such as the PDA peak area for an impurity (PDA_Area$_{impurity}$), to the mass-based peak area for the compound, such as the ELSD peak area for the impurity (ELSD_Area$_{impurity}$), divided by the ratio of the molar-based peak area for the reference compound, such as the PDA peak area for the API (PDA_Area$_{API}$), to the mass-based peak area for the reference compound, such as the ELSD peak area for the API (ELSD_Area$_{API}$). This is represented by the following expression, which is not correct.

$$RRF_{impurity} = \frac{\text{PDA\_Area}_{impurity}}{\text{ELSD\_Area}_{impurity}} \Big/ \frac{\text{PDA\_Area}_{API}}{\text{ELSD\_Area}_{API}} \text{ (incorrect equation)}$$

Figure 6A:
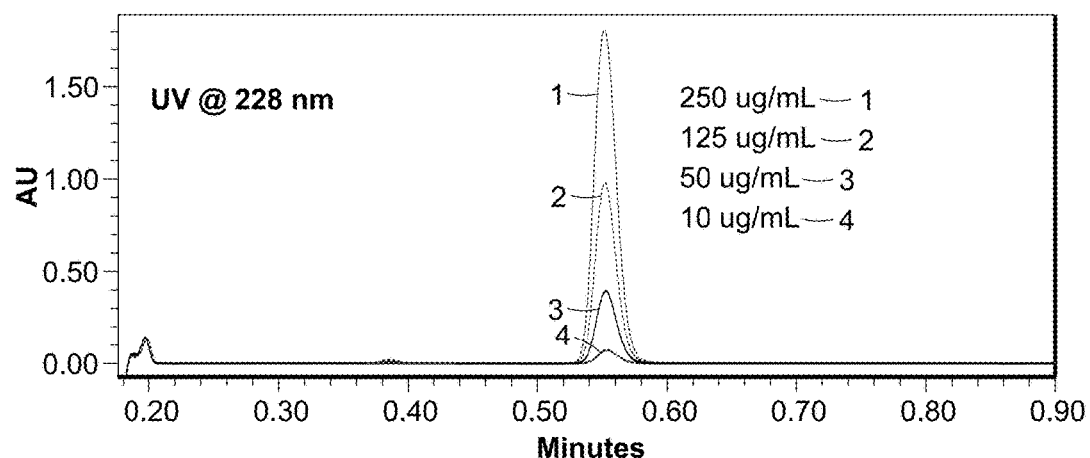
FIG. 6A is a graph of absorbance peak data for various concentrations of a compound.
Figure 6B:
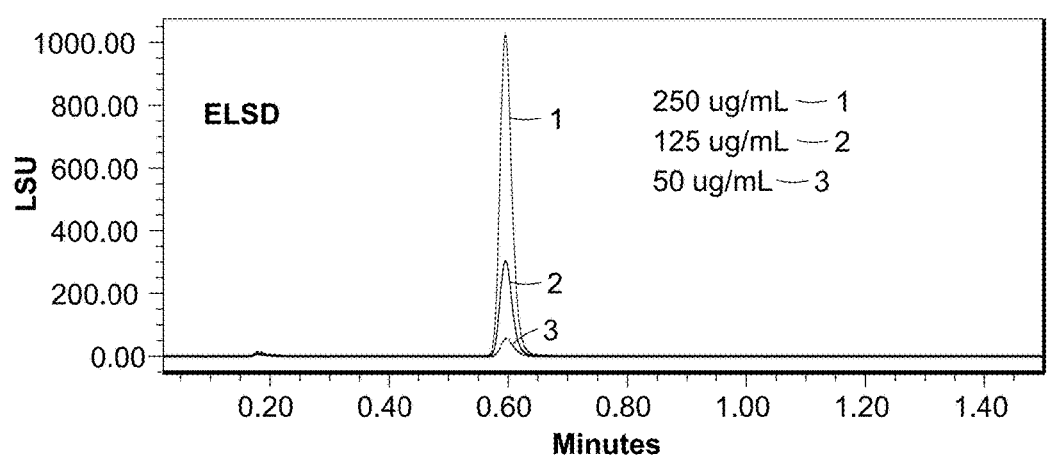
FIG. 6B is a graph of evaporative light scattering detector (ELSD) peak data for various concentrations of a compound.
Figure 6C:
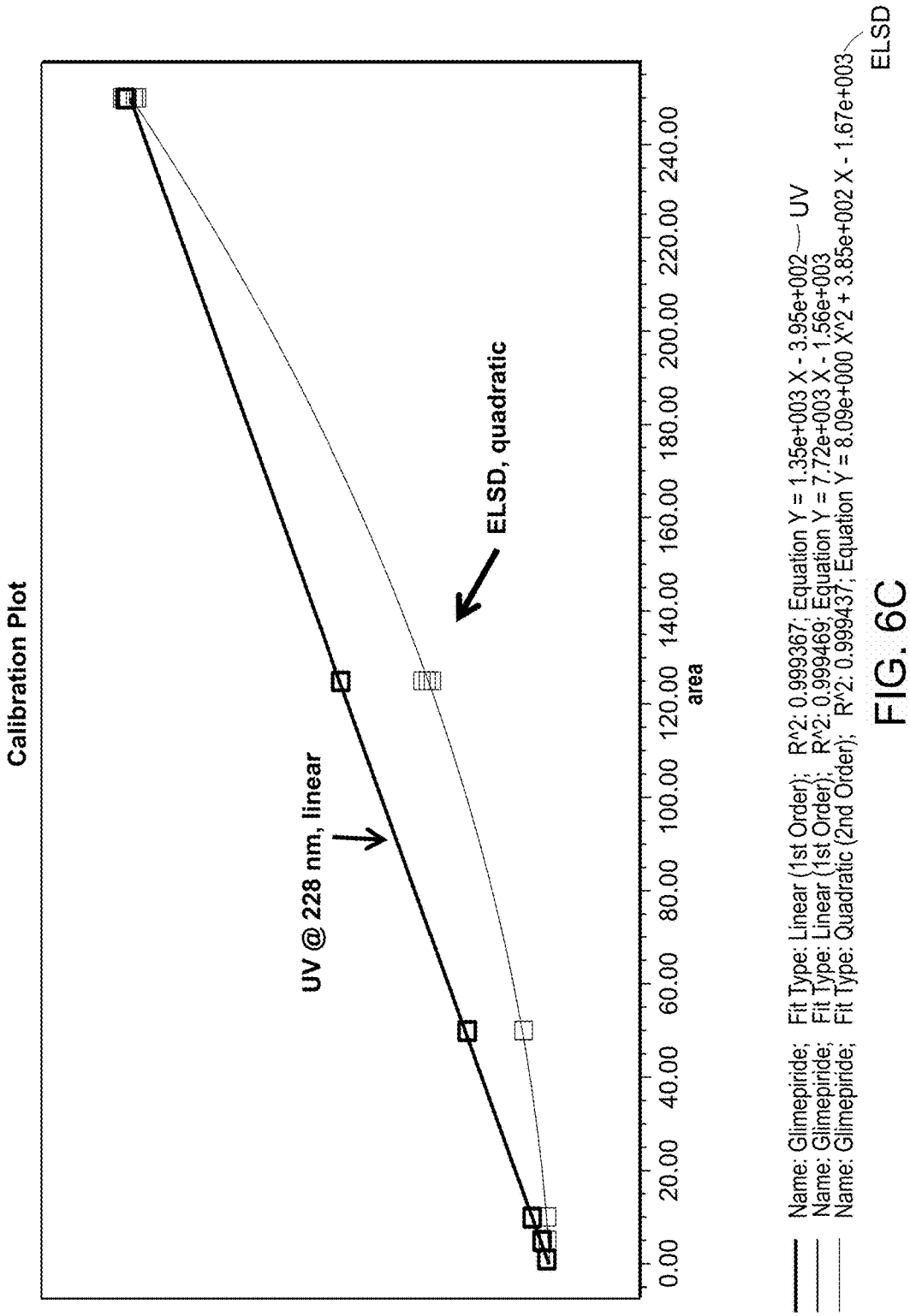
FIG. 6C is a graph of concentration versus peak area for absorbance data and ELSD data.

The inventors realized that the above equation does not accurately determine the RRF. FIG. 6A is a graph of PDA peaks in response to different concentrations of a compound and FIG. 6B is a graph of ELSD peaks in response to different concentrations of a compound. The PDA and ELSD responses do not scale in the same manner with concentration. This is clearly shown in FIG. 6C, which is a graph with markers indicating the concentration as a function of the area under the peak for PDA and ELSD. While the PDA shows a linear response for concentration versus peak area. ELSD demonstrates a logarithmic response. Use of the incorrect equation for RRF above, which assumes that the ELSD shows a linear response between peak area and concentration, produces RRF values that depart significantly from those obtained with the conventional calibration curve method of determining RRF. To illustrate this point, the inventors calculated RRF values using this incorrect equation and the data they obtained at two different wavelengths, 228 nm and 254 nm, with the results shown in the table below.

RRF Determinations Using Incorrect Equation

|  | 228 nm | | | 254 nm | |
| --- | --- | --- | --- | --- | --- |
| Amount | RRF Rel Compound B | RRF Rel Compound C | Amount | RRF Rel Compound B | RRF Rel Compound C |
| 50 | 0.37 | 0.49 | 50 | 0.36 | 0.48 |
| 125 | 0.37 | 0.46 | 125 | 0.36 | 0.46 |
| 250 | 0.37 | 0.48 | 250 | 0.41 | 0.25 |

As an illustrative comparison, the RRF for compound B at 228 nm was determined to be 1.36 using the conventional calibration curve method and was determined to be 0.37 using this incorrect equation. As another illustrative comparison, the RRF for compound C at 254 nm was determined to be 1.08 using the conventional calibration curve method and was determined to be between 0.25 and 0.48 using this incorrect equation.

Figure 7A:
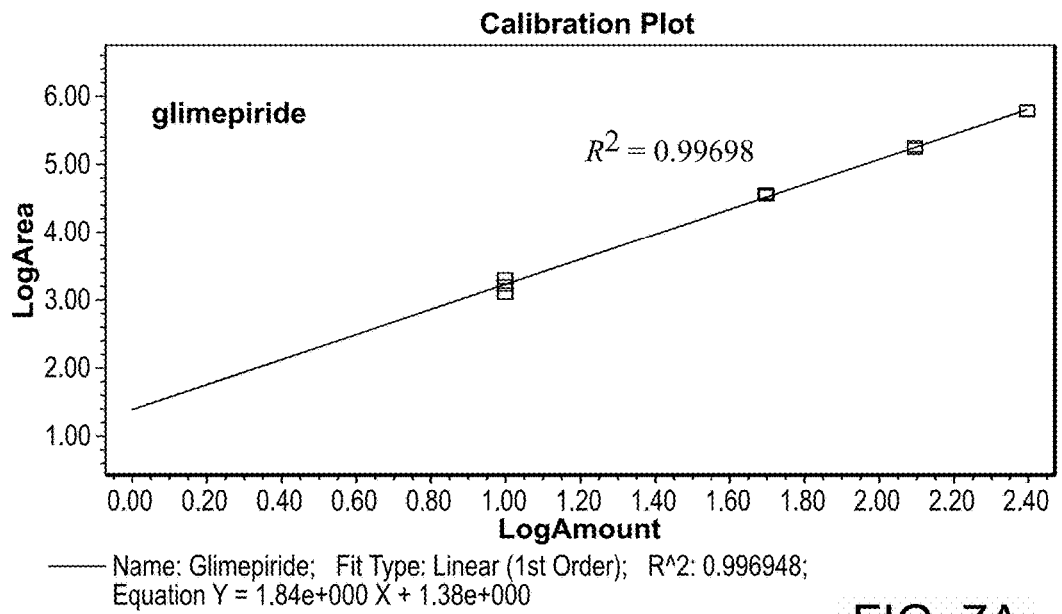
FIG. 7A is a graph of the log of peak area versus the log of concentration for ELSD data for an API.
Figure 7B:
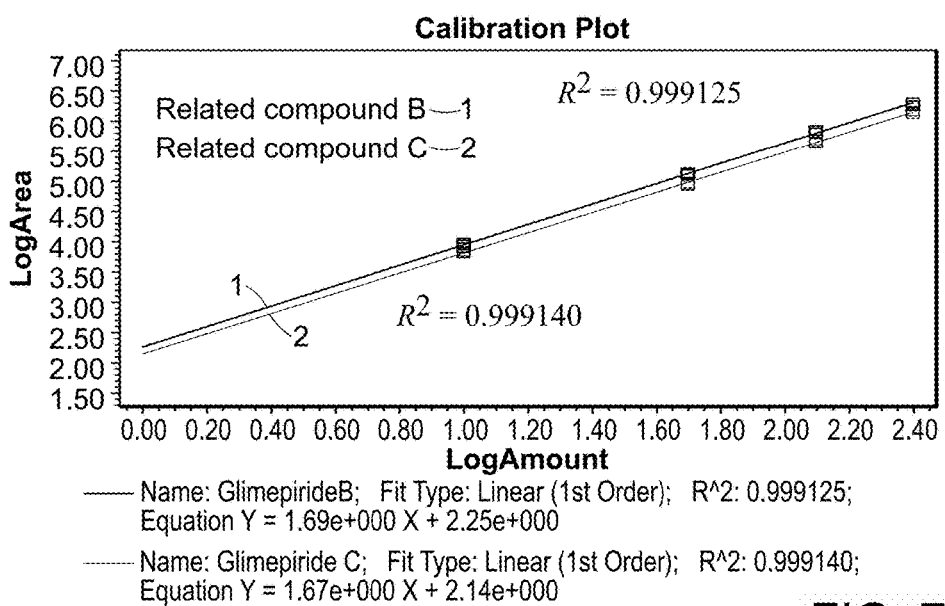
FIG. 7B is a graph of the log of peak area versus the log of concentration for ELSD data for impurities.

The inventor determined that the ELSD peak data exhibits a logarithmic response. FIG. 7A is a graph of the log of the ELSD peak area data as a function of the log of the concentration for the API glimepiride. FIG. 7B is a graph of the log of the ELSD peak area data as a function of the log of the concentration for impurities related compound B and related compound C. Both graphs include linear fits to the logarithmic data with $R^2$ values being close to 1 indicating that the logarithmic data is well fit by a linear function.

The inventors determined an accurate method of determining RRFs using orthogonal detection techniques. For this example, the inventors determined an RRF for an impurity based on the ratio of the PDA peak area for the impurity ($PDA\_Area_{impurity}$) to the logarithm of the ELSD peak area for the impurity ($ELSD\_Area_{impurity}$), divided by the ratio of the PDA peak area for the API ($PDA\_Area_{API}$), to the logarithm of the ELSD peak area for the API ($ELSD\_Area_{API}$). This is expressed in the following equation.

$$RRF_{impurity} = \frac{PDA\_Area_{impurity}}{\log(ELSD\_Area_{impurity})} \Big/ \frac{PDA\_Area_{API}}{\log(ELSD\_Area_{API})} \quad (6)$$

RRFs were determined under isocratic conditions at both 228 nm and 254 nm using the RRF equation 6 above with the results being shown in the table below.

RRF Determinations According to Exemplary Methods

|  | 228 nm | | | 254 nm | |
| --- | --- | --- | --- | --- | --- |
| Amount | RRF Rel Compound B | RRF Rel Compound C | Amount | RRF Rel Compound B | RRF Rel Compound C |
| 50 | 1.25 | 1.10 | 50 | 1.24 | 1.09 |
| 125 | 1.24 | 1.09 | 125 | 1.22 | 1.09 |
| 250 | 1.09 | 1.06 | 250 | 1.22 | 1.10 |

Comparison of the RRFs determined using exemplary methods with the RRFs determined using conventional calibration curve methods illustrates the high correlations between the two methods. Given the use of the conventional calibration curve method has been well established, these results indicate that the methods described herein for determining RRF using ratios of the PDA peak area to logarithmic ELSD peak area enable determination of RRF in a single analysis.

Degradation and Mass Balance

Figure 8:
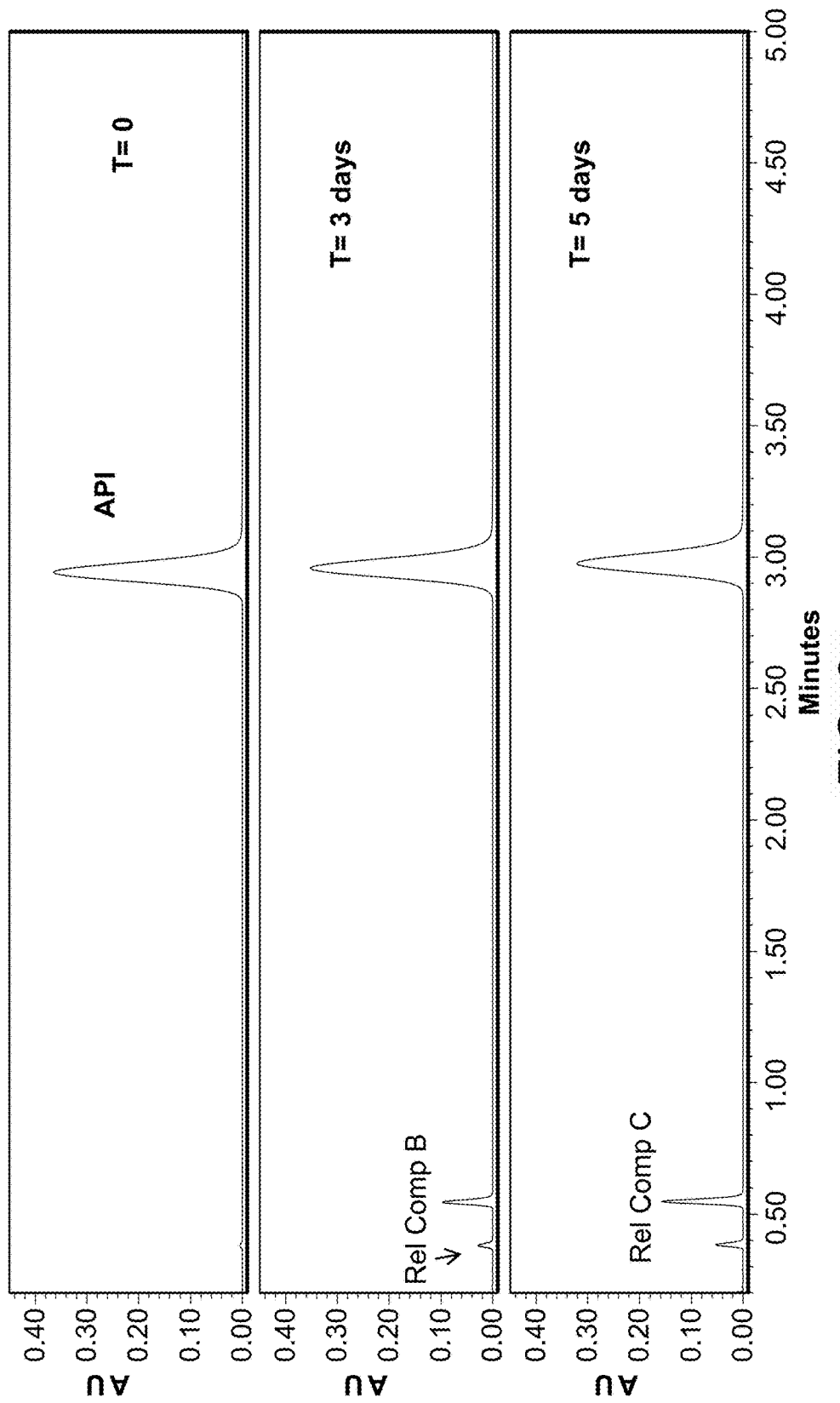
FIG. 8 include absorbance chromatograms for an initial sample including an API and samples after 3 days and 5 days of forced degradation.
Figure 9:
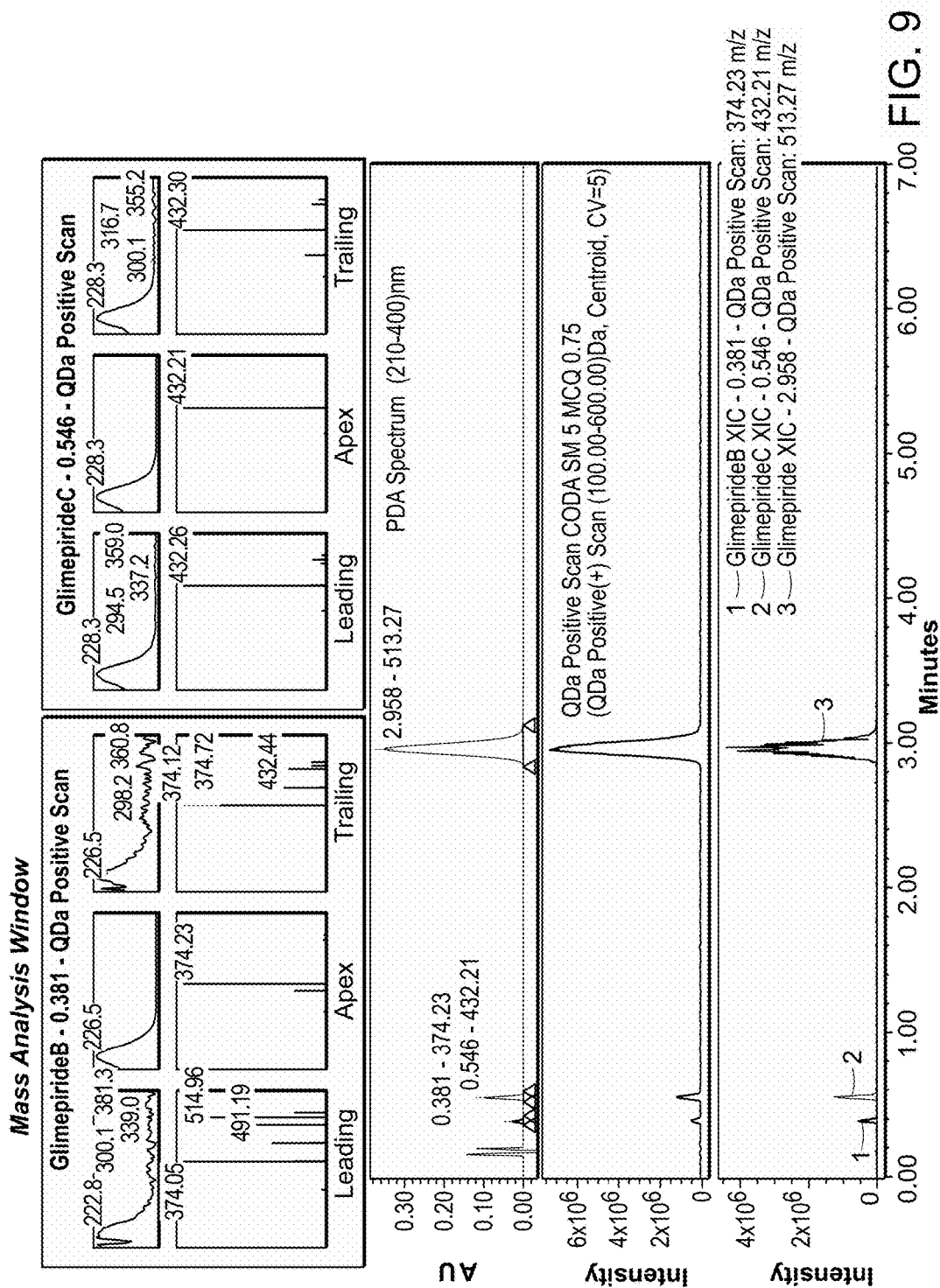
FIG. 9 includes graphical depictions of windows in a chromatographic software environment for confirming peak purity.
Figure 9:
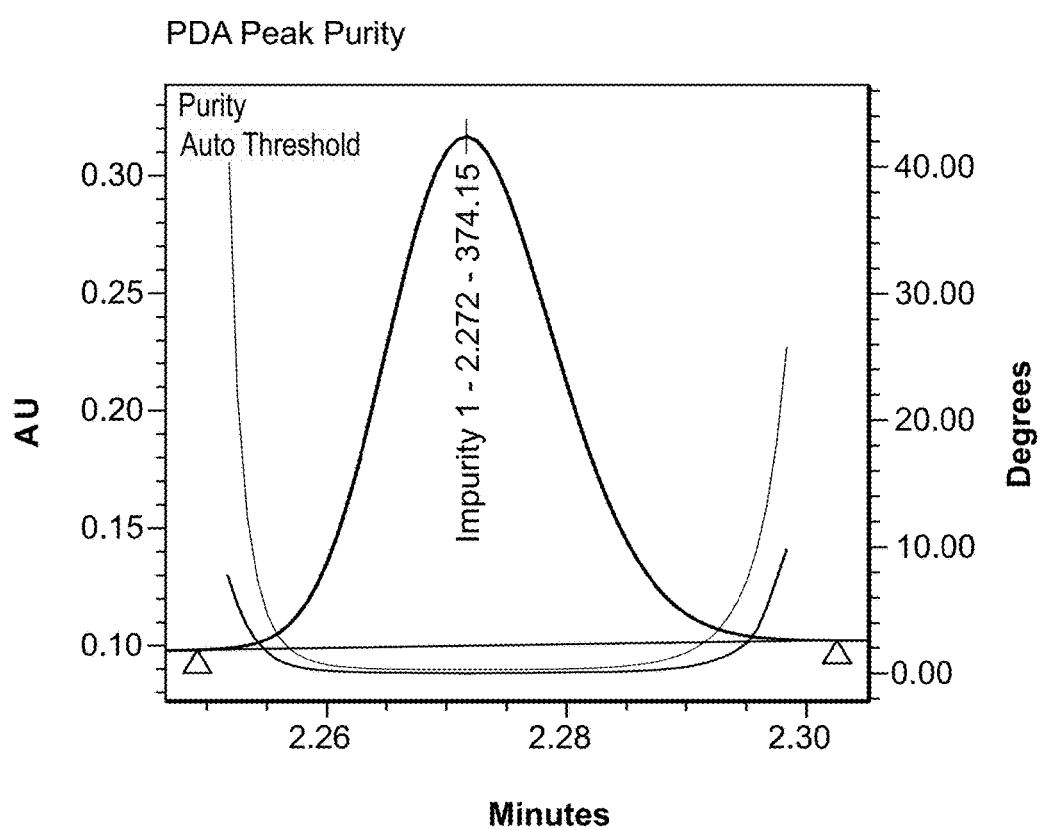

Acid hydrolysis was conducted on the drug substance (API) glimepiride over 5 days at 40° C. FIG. 8 shows the initial chromatogram and two subsequent chromatograms at 3 days and at 5 days. Two degradation impurities were present, which were labeled related compound B and related compound C. To ensure adequate separation and no co-elutions, peak purity was evaluated using a mass analysis window. FIG. 9 includes PDA peak purity and Mass analysis windows in the EMPOWER 3 data analysis software used to evaluate peak purity.

RRFs were calculated for the two impurities and the reciprocal of the RRF was used as a correction factor for each impurity to determine a corrected peak area for the impurity according to the following equation.

$$Corrected\_PDA\_Area_{impurity} = PDA\_Area_{impurity} * \frac{1}{RRF_{impurity}} = \quad (7)$$
$$PDA\_Area_{impurity} * Correction\_Factor_{impurity}$$

Within EMPOWER 3, the field named "Impurity RRF" corresponded to the correction factor so that the reciprocal of the RRF for the impurity was entered into this field. FIG. 10 includes two partial screen shots illustrating the correction factors applied to calculate corrected PDA peak areas within the EMPOWER 3 software.

A reference sample was run by HPLC and the total corrected PDA peak area was determined for the reference sample as described below. The correction factor of the reciprocal of the RRF for an impurity was used to determine a corrected PDA peak area for each impurity in the reference sample. The total corrected PDA peak area was the sum of the corrected PDA peak area for each impurity and the PDA peak area for the API glimepiride. This total corrected PDA peak is the value used to calculate percentage recovery.

$$\text{Total Corrected peak area} = \text{peak area}_{API} + \Sigma_{impurities}\text{Corrected peak area}_{impurity} \quad (8)$$

The degraded samples were run by HPLC and the correction factor of the reciprocal RRF for an impurity was used to obtain a corrected PDA peak area for each impurity in each degraded sample. For each degraded sample, a total corrected PDA peak area was calculated as the sum of the corrected PDA peak areas for the impurities and the PDA peak area for the API. The percentage recovery was the total corrected PDA peak area for the degraded sample divided by the total corrected peak are for the reference sample as indicated in the equation below.

$$\% \text{ recovery} = \frac{\text{Total Corrected peak area}_{degraded\ sample}}{\text{Total Corrected peak area}_{reference\ sample}} * 100 \quad (9)$$

Each peak area was determined based on the average of three different injections of the sample. The tables in FIG. 11 show example calculations of mass balance based on the experimental data.

Figure 12:
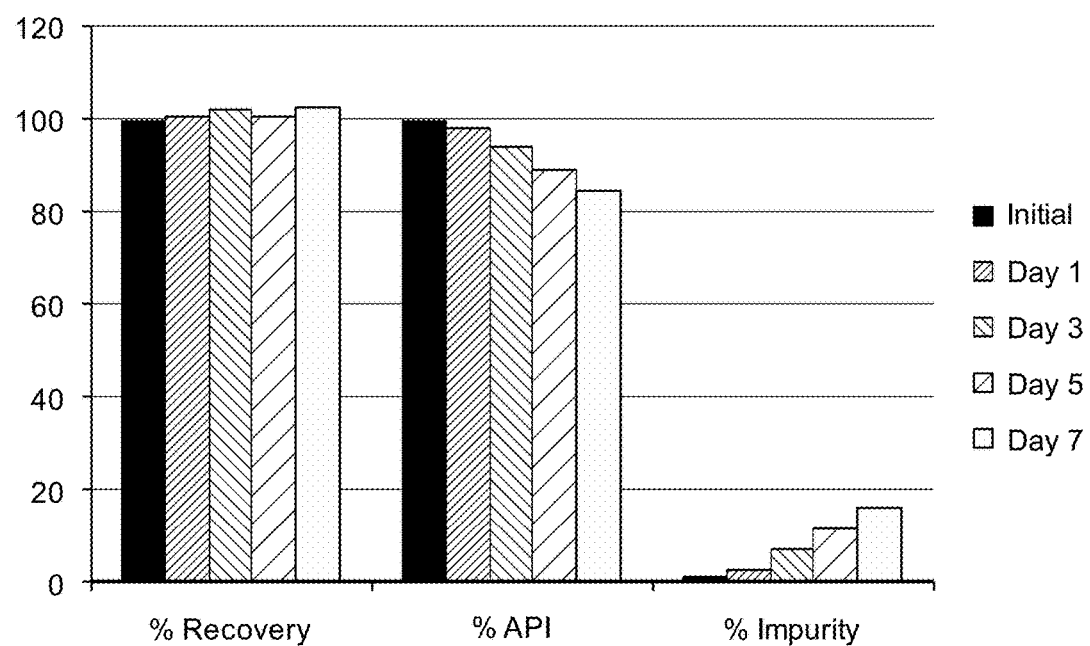
FIG. 12 includes a chart illustrating the mass balance calculation results, in accordance with some embodiments.

The results of the molar mass balance calculations of data from the forced degradation studies using the RRF calculated in accordance with embodiments described herein are summarized in the table below and are graphically depicted in a chart in FIG. 12. The percent recoveries ranged from 99 to 102.4%.

| n = 3 | Reference sample | T = 0 | 1 day | 3 days | 5 days | 7 days |
|---|---|---|---|---|---|---|
| Amount | 238.4 | 236.1 | 239.0 | 242.7 | 239.1 | 244.1 |
| Absolute Mass Balance Deficit | | 2.3 | −0.6 | −4.3 | −0.7 | −5.7 |
| % Recovery | | 99.0 | 100.2 | 101.8 | 100.3 | 102.4 |

Figure 13:
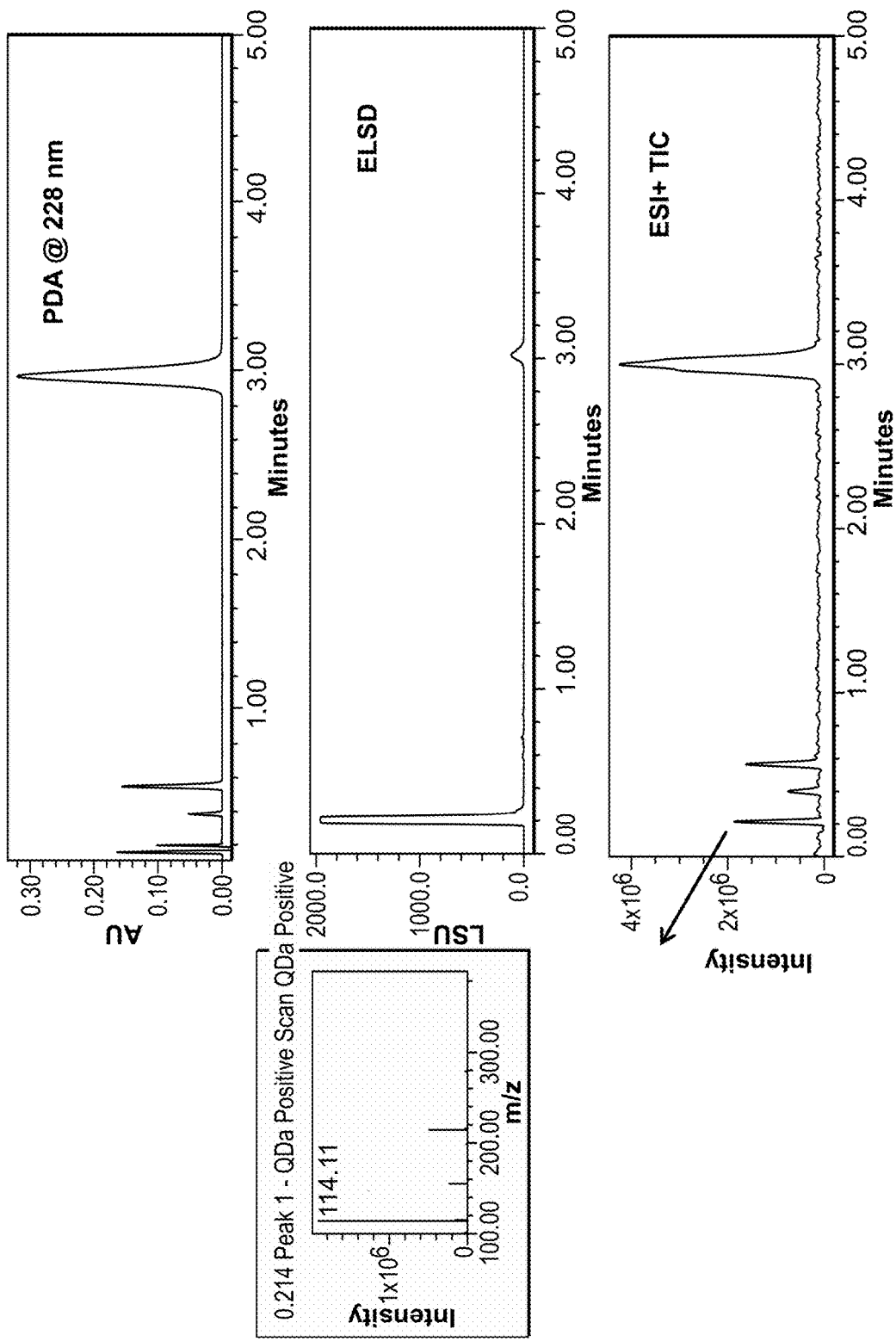
FIG. 13 includes chromatograms from a PDA detector (top) an ELSD (middle) and a mass detector (bottom), in accordance with some embodiments.
Figure 14:
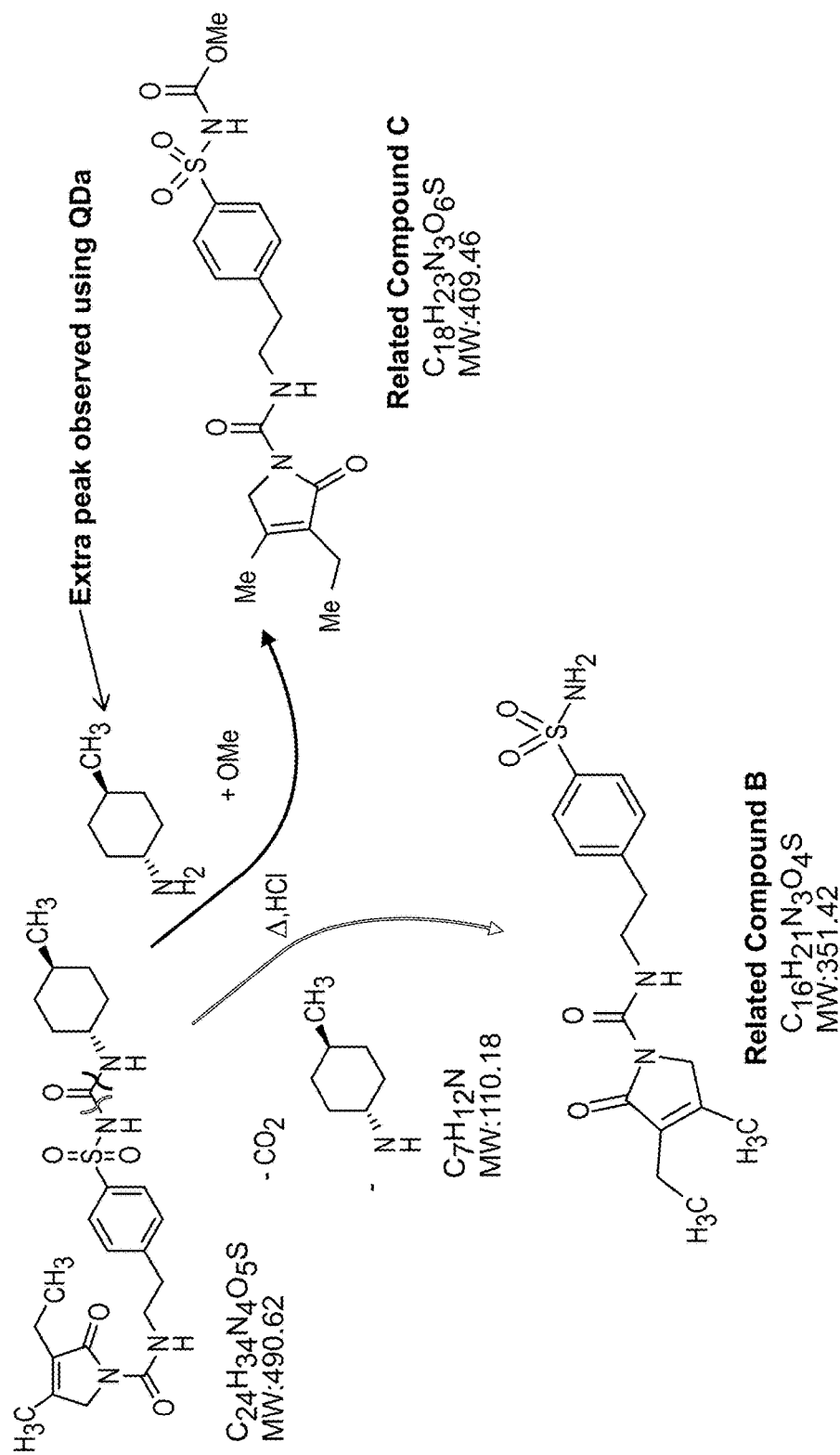
FIG. 14 schematically depicts a degradation pathway of glimepiride.

The chromatography system used for analysis included mass detection as well as UV-Vis absorption detection and ELSD. Although the mass detection was not required for determination of the RRFs, the mass detection was useful for providing additional information regarding degradation pathways. Further it enabled base mass labeling to aid in peak confirmation. FIG. 13 includes chromatograms from all three detectors, namely the PDA detector, the ELSD detector and the mass detector. The mass detector also enable detection of analytes that do not have a chromophore. FIG. 14 shows the degradation pathway of glimepiride. The mass detector identified an extra peak corresponding to an additional molecule (a byproduct) involved in the degradation pathway, which could not be observed with the PDA or the ELSD because it did not include a chromophore.

Conclusions

RRFs were determined for impurities based on ratio of the PDA peak area for the impurity to the logarithm of the ELSD peak area for the impurity, divided by the ratio of the PDA peak area for the API, to the logarithm of the ELSD peak area for the API. The RRFs determined by this method were consistent with RRFs calculated using the conventional calibration curves and standards method. The RRFs determined with the inventors' method were successfully used for mass balance in a forced degradation study of the API glimepiride. In contrast with the RRFs determined using the conventional calibration curves and standards method, the RRFs calculated with the inventors' method did not require obtaining standards for the API and each impurity and multiple calibration runs with samples having different known concentrations of each. In contrast to the conventional calibration curve method for determining RFFs, the inventor's method of determining RRF can be determined using testing includes orthogonal detection with both a molar concentration-based detector (e.g., a UV-Vis absorption) and a mass concentration-based detector (e.g., ELSD) conducted on a single sample.

Example 2

In Example 2 the inventors conducted another determination of relative response factors (RRFs) and mass balance for degradation of glimepiride using both a conventional method for determining RRFs requiring the generation of calibration curves using samples with known concentrations of the compounds of interest, and using a method for determining RRF according to embodiments described herein. After performing Example 1, the inventors determined that the extra peak in the mass spectroscopy data corresponding to an additional molecule (a byproduct) involved in the degradation pathway, which could not be observed with the PDA or the ELSD, was 4-methylcyclohexamine. In Example 2 the inventors included this additional molecule in the analysis and in the comparison with the conventional RRF technique conducted more detailed degradation analysis.

Experimental Apparatus and Conditions

The chromatographic system was an ultra-high performance liquid chromatography system, specifically, an ACQUITY UPLC H-Class system with a pump (ACQUITY Quaternary Solvent Manager (QSM)), an injector (ACQUITY Flow Through Needle (FTN) Autosampler) and a column manager (ACQUITY Column Manager). The autosampler was configured with a 50 µL extension loop. The seal wash was 90:10 water/methanol, purge solvent was methanol and the needle wash solvent was 0.1% (v/v) formic acid in 30:70 water/acetonitrile. Detection was performed with a photodiode array detector (ACQUITY UPLC PDA), an evaporative light scattering detector (ACQUITY UPLC ELSD) and a mass detector (ACQUITY QDa) (Waters, Milford, Mass.). The eluent flow path was plumbed from the column to a triple static tee (1:10 split flow) housed within a secondary pump (ACQUITY Isocratic Solvent Manager (ISM)). The tubing from the column to the tee was 22.5" of 0.004" ID tubing. In the first split, a portion of the flow was diverted to the PDA with 16" of 100 µm ID fused silica tubing and then, in series, to the ELS detector with 12" of 0.004" ID PEEK tubing. Flow from the isocratic solvent manager was introduced into the second splitter, and the final portion of flow was diverted to the mass spectrometer via the detector probe (250 mm). The chromatography data system was Empower 3 FR3 (Waters, Milford, Mass.). The forced degradation was performed using a water bath (Isotemp) purchased from Fisher Scientific.

The separation of glimepiride and related compounds B and C was achieved on a 2.1 mm×50 mm, 1.8 µm, ACQUITY UPLC HSS T3 $C_{18}$ column (Waters Corporation) under isocratic conditions. The mobile phase was 0.1% (v/v) formic acid in 60:40 water/acetonitrile at a flow rate of 0.8 mL/min. The column temperature was 30° C. with mobile phase pre-heating. Injection volume was 4 µL. The PDA settings included wavelength of 228 nm, sampling rate of 20 points per second. The ELSD was set to a gas pressure of 25 psi, the nebulizer in Cooling mode, drift tube temperature of 55° C. and the gain set to 100 with a data rate of 10 points per second. The make-up pump was used for post-column addition of solvent using the ISM at a flow rate of 0.3 mL/min with 0.1% (v/v) formic acid in methanol. The mass detector (ACQUITY QDa, Waters Corp, USA) utilized positive electrospray ionization (ESI+), with a cone voltage set to 5 V. The capillary voltage was 1.4 kV and the sampling rate was 5 points per second. The mass range collected was 100-600 Da with additional single ion recording (SIR) channels were collected simultaneously for the following m/z=114.1 Da, 374.6 Da, 432.2 Da and 513.7 Da. The SIR channels were measured with a cone voltage of 5 V.

Sample and Standards Preparation

Standards were prepared for conventional RRF determination by LC-PDA. A solution of glimepiride and related impurities were each individually prepared at a concentration of 0.4 mg/mL in methanol. All samples were sonicated for 10 minutes to ensure complete dissolution. Working standards were then prepared by diluting the stock with 25:75 water/methanol. For glimepiride (API), individual calibration standards were prepared in triplicate at 0.05% (w/w), 0.1%, 0.3%, 0.4%, 0.5%, 1%, 10%, 20%, 40% and 100% of the sample concentration of 0.250 mg/mL. Related compound B and related compound C standards were prepared individually in triplicate at 0.05%, 0.1%, 0.3%, 0.4%, 0.5%, 1%, 10%, 20% and 40% of 0.250 mg/mL. The labeled purity of glimepiride was 99.6% and that of each related compounds was 100%.

Working standard solutions were also prepared for conventional RRF determination by LC-PDA-ELSD. Specifically, working standard solutions were prepared containing all three compounds, glimepiride and related compounds (B and C). Working standards were prepared in triplicate at 10% (w/w), 20%, 30% and 50% of 0.250 mg/mL with a final diluent composition of 25:75 water/methanol.

Additionally, standards of 4-Methylcylohexylamine for quantitation by mass spectrometry. Specifically, a solution of 4-methylcylcohexylamine was prepared at a concentration of 0.4 mg/mL in 25:75 water/methanol. Working standards were then prepared by diluting the stock with 25:75 water/methanol. Individual calibration standards were prepared in triplicate at 0.04% (w/w), 0.2%, 0.5%, 1%, 2% and 5%, of the sample concentration of 0.250 mg/mL. The labeled purity of 4-methylcylcohexylamine was 99.7%.

Results and Discussion

A relative response factor as defined by the USP is the response of the impurity to that of the API. As noted above, the conventional method to determine the RRF using LC-UV uses the ratio of the slope of the calibration curve of the impurity to that of the API. In these evaluations, consideration must be given to the concentration ranges in the experiment. For example, in force degradation studies, the goal of the analysis is to achieve 10-15% degradation. During analysis, the limit of detection required for the impurities should also be considered. Typical impurity reporting thresholds are often 0.05% of the active pharmaceutical, therefore the calibration curves were tested over the range of 0.05% to 20% for the impurities and 0.05% to 100% for the active pharmaceutical ingredient.

The calibration curves for glimepiride and related impurities met correlation coefficients ($R^2$) values of greater than 0.995, with 1/x weighting applied. The signal to noise (S/N) for the lowest calibration point was greater than 10, thus suggesting an operating range for the RRF determinations greater than the limit of quantitation as defined by the USP.

For the PDA data, the RRF factors were calculated based on the response of the impurity relative to that of the main component using the ratio slope of the calibration curve for the impurity to that of the active pharmaceutical ingredient (see equation 2 above).

The calibration curve slopes from the PDA data and resulting calculated RRF values using conventional methods appear in the table below.

PDA Calibration Curve for Glimepiride and Related Compounds

| Compound | n | fit | weighting | y | slope (b) | $R^2$ | RRF |
|---|---|---|---|---|---|---|---|
| Glimepiride | 10 | linear | 1/x | 3530 | 16088 | 0.999391 | 1.00 |
| Related Compound B | 9 | linear | 1/x | −110 | 21421 | 0.999167 | 1.32 |
| Related Compound C | 9 | linear | 1/x | 1550 | 18534 | 0.999315 | 1.15 |

To evaluate the feasibility of the orthogonal detection approach, working standards containing glimepiride and the related compounds were run on a UV-ELSD system, connected in series. The calibration standards were prepared in triplicate at 10% (w/w), 20%, 30%, 40% and 50% of the assay value (0.250 mg/mL). Higher values were used for the analysis by UV-ELSD combination than the previous method described due to the sensitivity constraints of ELS detection.

Figure 15A:
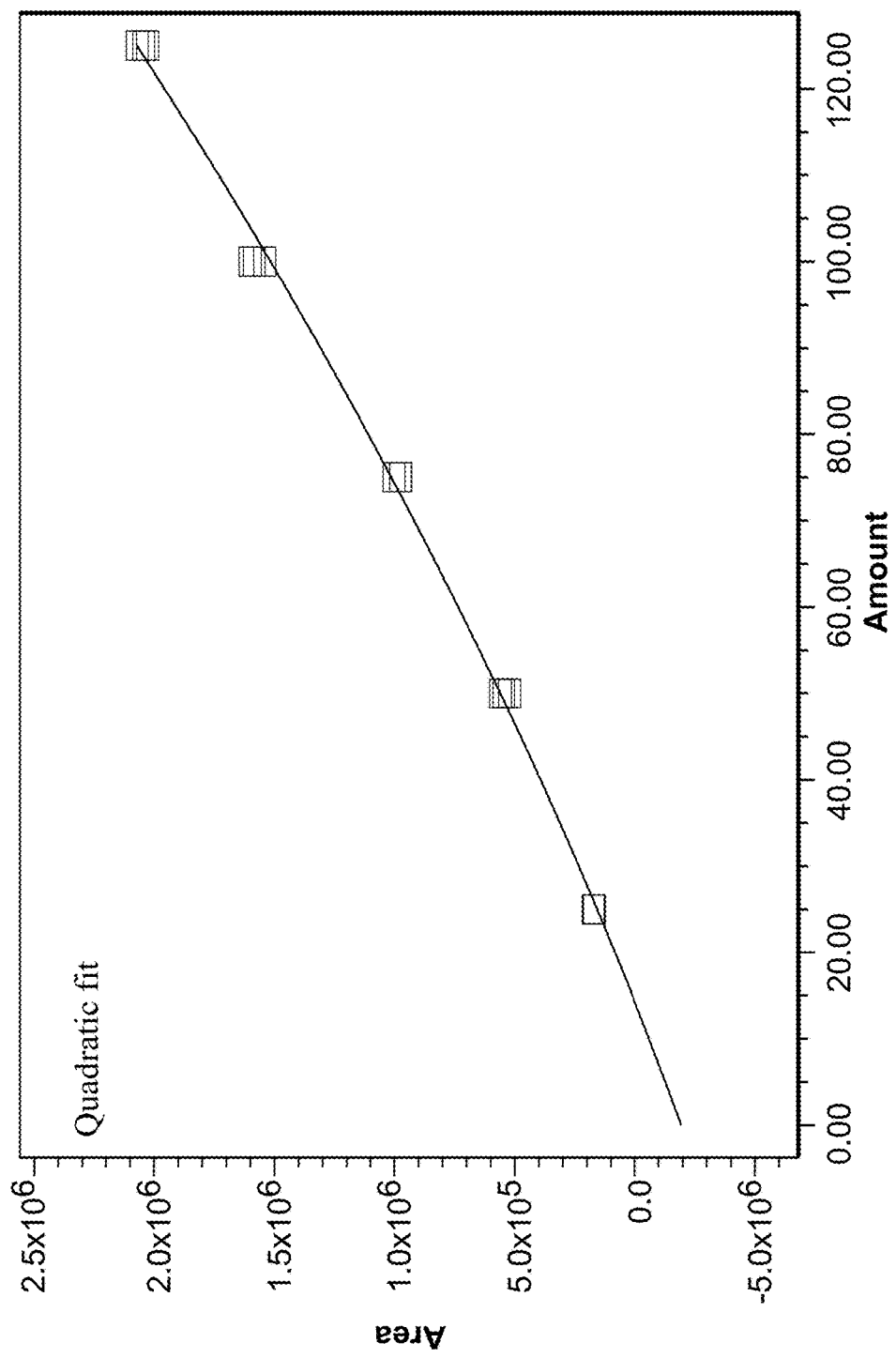
FIG. 15A includes an ELSD Calibration curve for a glimepiride related compound.

The resulting calibration curves showed a non-linear response in the ELSD (FIG. 15A) with the response in the evaporative light scattering detector based on the non-linear function:

$$A = a \times m^b \quad (10)$$

where A is area, m is the mass and a and b are coefficients that are dependent on various factors, including the detector characteristics, mobile phase conditions, and the size and shape of the particles analyzed by light scattering. This function can also be represented using the log-log function:

$$\log A = b \log m + \log a \quad (11)$$

Figure 15B:
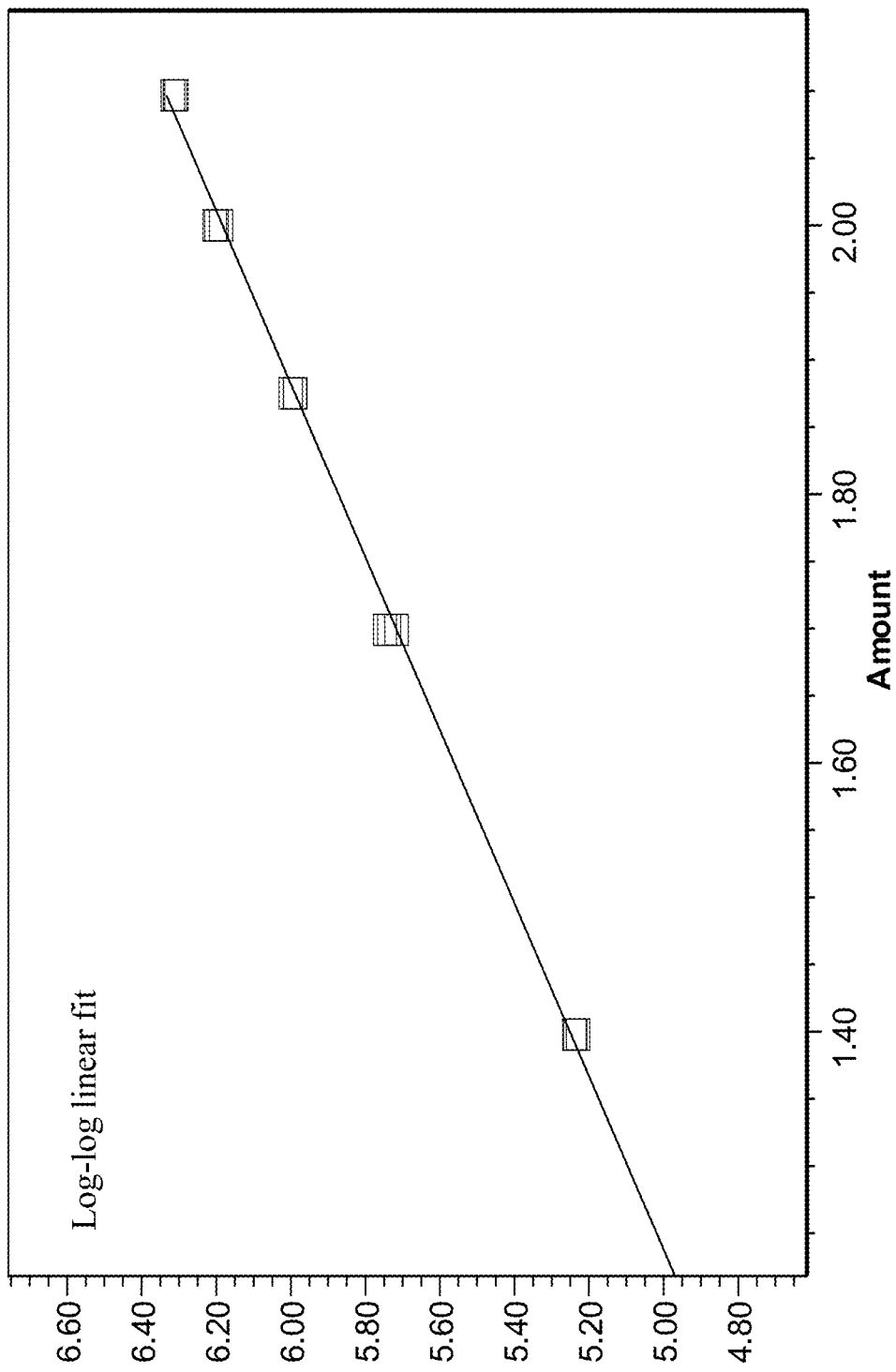
FIG. 15B includes log-log linear fit for an ELSD calibration curve for a glimepiride related compound.

The log-log transformation of the results allows a linear calibration curve to be plotted (FIG. 15B). Applying this principle to the previously described experiment, the log-log results achieve a linear calibration curve (Table 2). The linear calibration curves for glimepiride and related impurities met correlation coefficients ($R^2$) values of greater than 0.995. The calibration curve slopes from log-log fit to the ELSD data for glimepiride and related compounds B and C appear in the table below.

ELSD Calibration Curve (Log-Log Fit) for Glimepiride and Related Compounds

| Compound | n | fit | weighting | y intercept (log a) | slope (b) | a | $R^2$ |
|---|---|---|---|---|---|---|---|
| Glimepiride | 5 | Log-log linear | none | 2.33 | 1.69 | 213 | 0.996650 |
| Rel Cmpd B | 5 | Log-log linear | none | 3.08 | 1.55 | 1202 | 0.998007 |
| Rel Cmpd C | 5 | Log-log linear | none | 2.90 | 1.57 | 794 | 0.996128 |

RRFs were also calculated using orthogonal detection techniques instead of using slopes of calibration curves. Using equation 6 above and data from both UV (e.g., PDA) and ELSD detection, RRF response ratios were obtained for the standards over the concentration ranges (10-50% (w/w). The values obtained are shown in the table below.

Relative Response Ratios Determined by UV-ELSD

| Standard Concentration (w/w) | Sample Number | RRF Rel Cmpd B | RRF Rel Cmpd C |
|---|---|---|---|
| 10% | 1 | 1.26 | 1.13 |
| 10% | 2 | 1.23 | 1.11 |
| 10% | 3 | 1.25 | 1.11 |
| 20% | 4 | 1.26 | 1.11 |
| 20% | 5 | 1.23 | 1.09 |
| 20% | 6 | 1.23 | 1.10 |
| 30% | 7 | 1.26 | 1.10 |
| 30% | 8 | 1.25 | 1.11 |
| 30% | 9 | 1.26 | 1.11 |
| 40% | 10 | 1.24 | 1.10 |
| 40% | 11 | 1.24 | 1.10 |
| 40% | 12 | 1.24 | 1.11 |
| 50% | 13 | 1.29 | 1.17 |
| 50% | 14 | 1.26 | 1.11 |

-continued

| Standard Concentration (w/w) | Sample Number | RRF Rel Cmpd B | RRF Rel Cmpd C |
|---|---|---|---|
| 50% | 15 | 1.25 | 1.11 |
| Mean | | 1.25 | 1.11 |
| Std Dev | | 0.017 | 0.018 |
| % RSD | | 1.34 | 1.65 |

These RRF values were compared to the method previously described using the slopes of the calibration curves using UV (e.g., PDA) data, the latter of which is considered standard. The mean RRF value obtained for related compound B and related compound C using the UV-ELSD detection were 1.25 and 1.15 respectively. These values correlate fairly well to those determined from the UV (e.g., PDA) data and the conventional method of determining RRF, specifically 1.32 for related compound B and 1.15 for related compound C, indicating the utility of this approach.

To further explore the possibility of using this RRF approach with a degraded drug substance or API, acid hydrolysis was conducted under accelerated conditions, specifically, at 80° C. The objective of this experiment was to produce both impurities and API in sufficient quantities to analyze all compounds by both ELS and PDA detection techniques. Using equation 6 and the UV and ELSD peak areas, the RRFs were calculated for both related compound B and C. In addition, various time points were analyzed to evaluate the effect of impurity/API concentration on the calculations. The results are shown in the table below.

Relative Response Factors Determined by
LC-PDA-ELSD with Accelerated Degradation of
Drug Substance

| Time (min) | Replicates | RRF Rel Cmpd B | RRF Rel Cmpd C |
|---|---|---|---|
| 30 | 3 | 0.13 | 0.42 |
| 60 | 3 | 0.79 | 1.30 |
| 90 | 3 | 1.48 | 2.34 |
| 120 | 3 | 1.89 | 2.09 |

Figure 16:
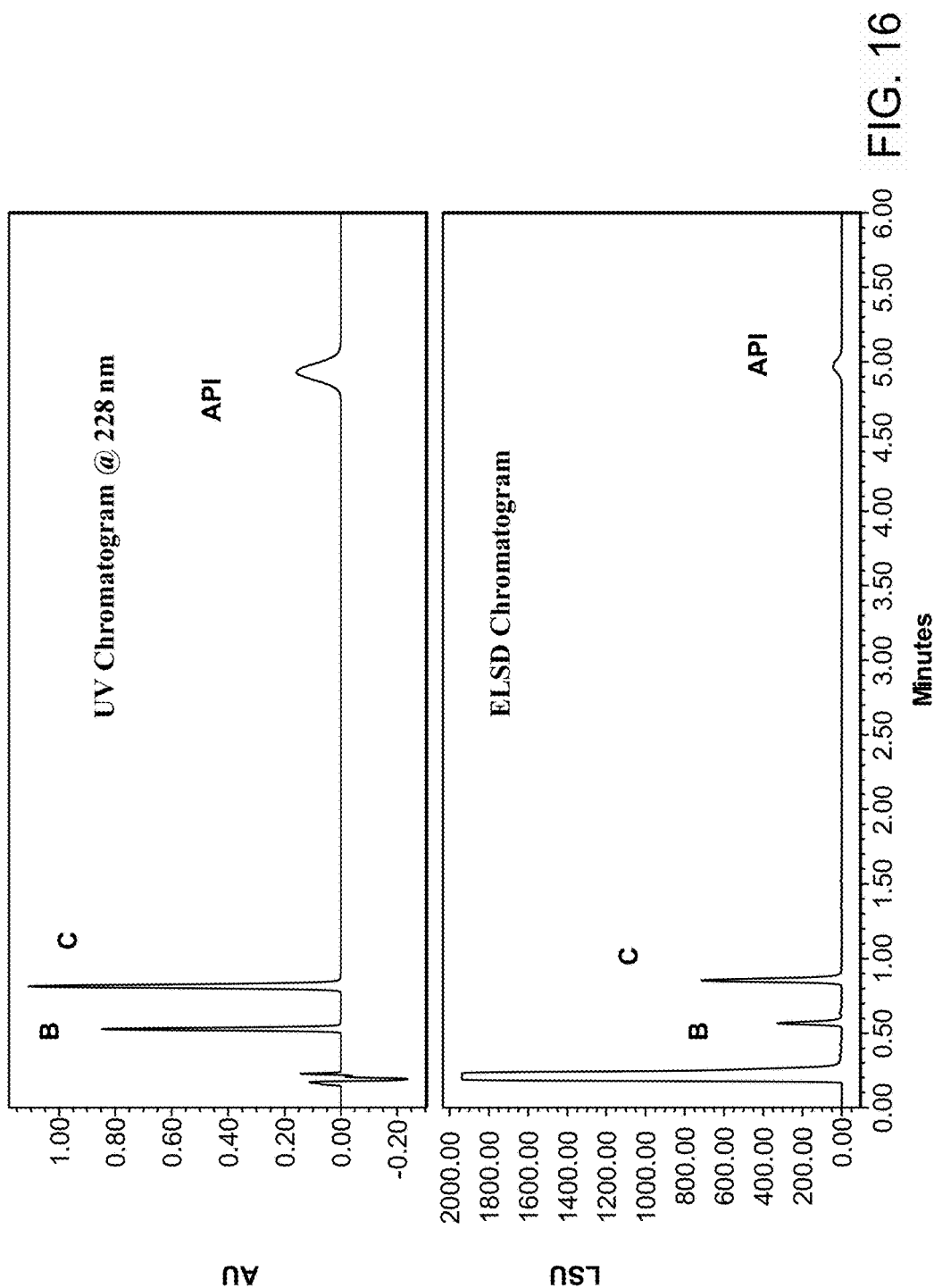
FIG. 16 includes chromatograms for accelerated forced degradation of the glimepiride drug substance by acid hydrolysis at 1 hour at 80° C. Stacked plot of UV (top) and ELSD (bottom) chromatograms show the differences in response for impurities as well as the drug substance.

At 1 hour (FIG. 16), the RRF for related compound C was comparable to that obtained using the slopes of the calibration curves at 1 hour (1.30 vs. 1.11), while the results for related compound B were significantly lower (0.79 vs 1.25). However, with 90 min of heating, a higher concentration of related compound B was produced and the RRF calculated was comparable to the previous method (1.48 vs. 1.25). The results indicate comparable amounts of both the API and related compound must be present for this approach to provide a reasonable value for estimation of the RRF During acid hydrolysis of glimepiride, related compound C was the primary degradant, while related compound B was formed in lower quantities. Therefore, a sufficient concentration for reliable determination of the RRF using this approach was reached earlier in the degradation process for related compound C than for related compound B.

These results demonstrated the ability of the orthogonal detection LC-PDA-ELS approach to estimate the RRF ratios of impurities provided that the related impurity is present in sufficient quantities for reliable detection in ELSD. However, during forced degradation of a drug substance or product, it can be difficult to achieve the concentration of both the API and the impurities for quantitation in the molar-mass based detector. Furthermore, non-chromophoric species in a drug substance or drug product can impact the separation and quantitation in ELS detection and should be considered when the analysis is performed on other active pharmaceutical ingredients. Lastly, the formation of very different sized particles can impact the relationship of the API and related impurities. Specifically, the size(s) and shape of the particles impact the light-scattering mechanisms (Rayleigh-Debye, Mie and refraction-reflection). Therefore, particles of very different size may not give comparable responses or relative response required for these analyses.

To demonstrate the impact RRF have on the relative quantitation of impurities and mass balance calculations, the drug substance was exposed to degradation conditions. Over a period of 7 days, the drug substance was exposed to acidic, basic and oxidative conditions with goals of achieving approximately 10% degradation as quantified by UV. The samples were tested at 2 day intervals and analyzed by UV-ELS and MS.

Figure 17:
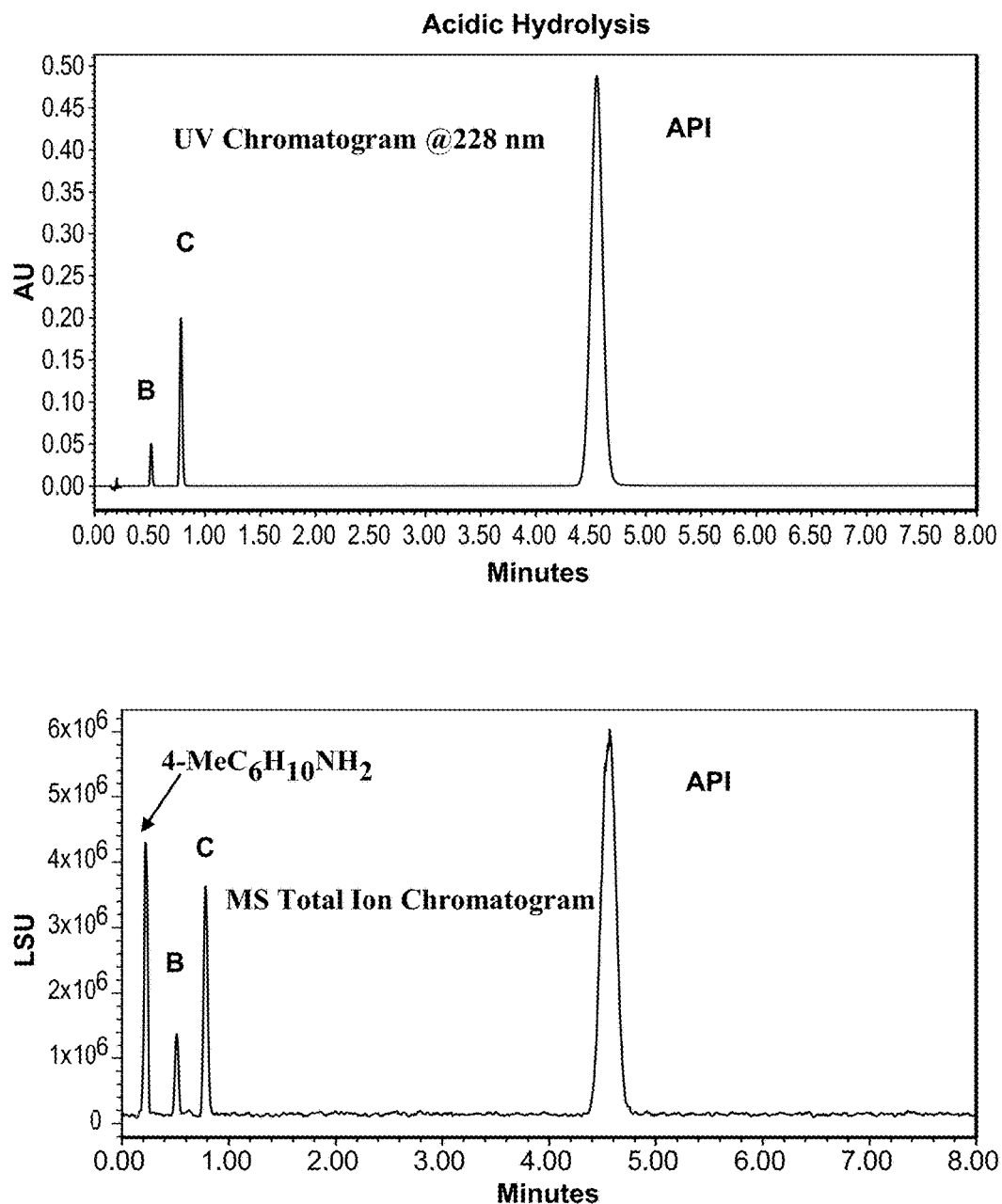
FIG. 17 includes chromatograms for acid hydrolysis of the glimepiride drug substance at 5 days. UV chromatogram (228 nm) (top) shows the presence of related compound B (B) and related compound C (C) as well as the drug substance, glimepiride (API). The MS, Total Ion Chromatogram (TIC), (bottom) shows the presence of an additional peak eluting prior to related compound B. The mass spectrum for this analyte shows a predominant m/z of 114.1, which corresponds to the by-product formed in the degradation reaction or 4-methylcylcohexylamine.

Acidic hydrolysis of glimepiride produced two impurity peaks, related compound B and C, which were found to increase over the time period with 16.69% impurities achieved at 7 days. FIG. 17 shows a UV chromatogram and an MS Total Ion Chromatogram (TIC) from acid hydrolysis of glimepiride at 5 days. Confirmation of the impurities was provided by the mass spectrometry. The degradation conditions resulted in the formation of sodium adducts in MS for related compounds B and C, as well as glimepiride as shown in the detailed spectra of peaks in MS, TIC in FIG. 18. The evaporative light scattering detector also showed the presence of an additional peak, eluting just prior to related compound B. Evaluation of the mass spectrum shows a m/z=114.1 Da, corresponding to the by-product, 4-methylcylcohexylamine, formed in the formation of both related compound B and C.

Figure 19:
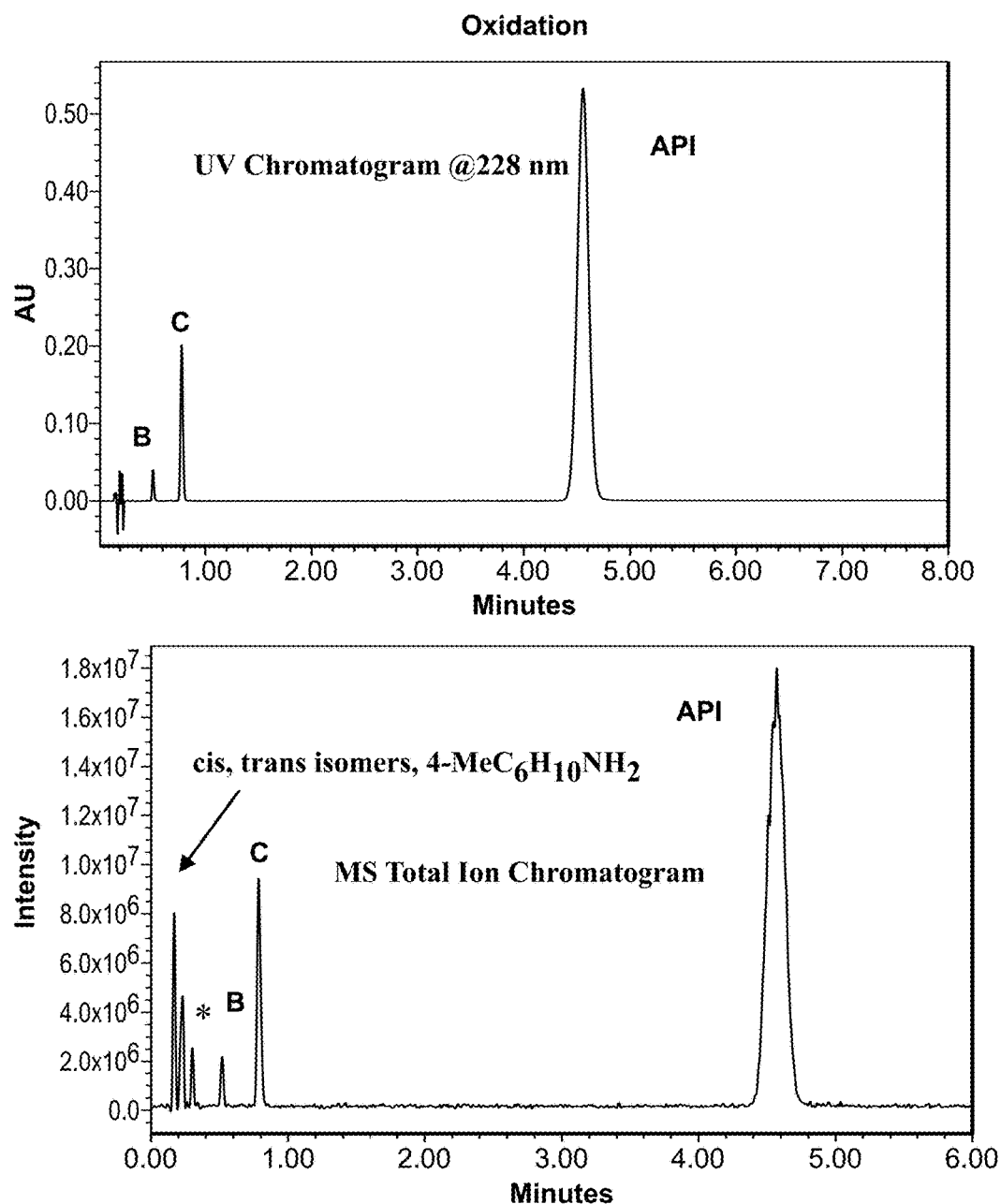
FIG. 19 includes chromatograms for oxidation by azobisisobutyronitrile (AIBN) of the glimepiride drug substance at 5 days. UV chromatogram (228 nm) (top) shows the presence of related compound B (B) and related compound C (C) as well as the drug substance, glimepiride (API). The MS, (Total Ion Chromatogram (TIC), (bottom) shows the presence of three additional peaks eluting prior to related compound B. The mass spectrum for the first two partially separated peaks showed a predominant m/z of 114.1, which corresponds to the cis- and trans-isomers of the by-product formed in the degradation reaction or 4-methylcylcohexylamine. The third peak is a product of the AIBN oxidation (m/z 177.1)-*-, as evidenced by analysis of the control.

Under oxidative conditions, a similar chromatographic profile was observed in UV as that observed under acidic conditions, however, additional peaks were observed in the mass spectrum. For example, FIG. 19 includes chromatograms from analysis of a glimepiride drug substance after 5 days of oxidation by AIBN. The UV chromatogram (228 nm) shows the presence of related compound B (B) and related compound C (C) as well as the drug substance, glimepiride (API). The MS, Total Ion Chromatogram (TIC) shows the presence of three additional peaks eluting prior to related compound B. The mass spectrum for the first two partially separated peaks shows a predominant m/z of 114.1, which corresponds to the cis- and trans-isomers of the by-product formed in the degradation reaction or 4-methylcylcohexylamine. The third peak is a product of the AIBN oxidation (m/z 177.1)-*- as evidenced by analysis of the control. One of the unknown peaks present in the AIBN control (m/z=177.2 Da) was attributed to the reagent. As observed with the acidic hydrolysis of glimepiride, the by-product (m/z=114.1 Da) was also observed. In addition, the oxidation degradation produced two isobaric peaks as determined by the QDa measurement resulting in the same m/z values. The standard for 4-methylcylcohexylamine, a combination of the cis- and trans-isomer, also revealed the presence of two peaks. Thus, comparing the mass spectrum of the standard indicated that under oxidative conditions, both isomers of the by-product are formed, however, under acidic hydrolysis conditions only a single isomer is formed.

Figure 20:
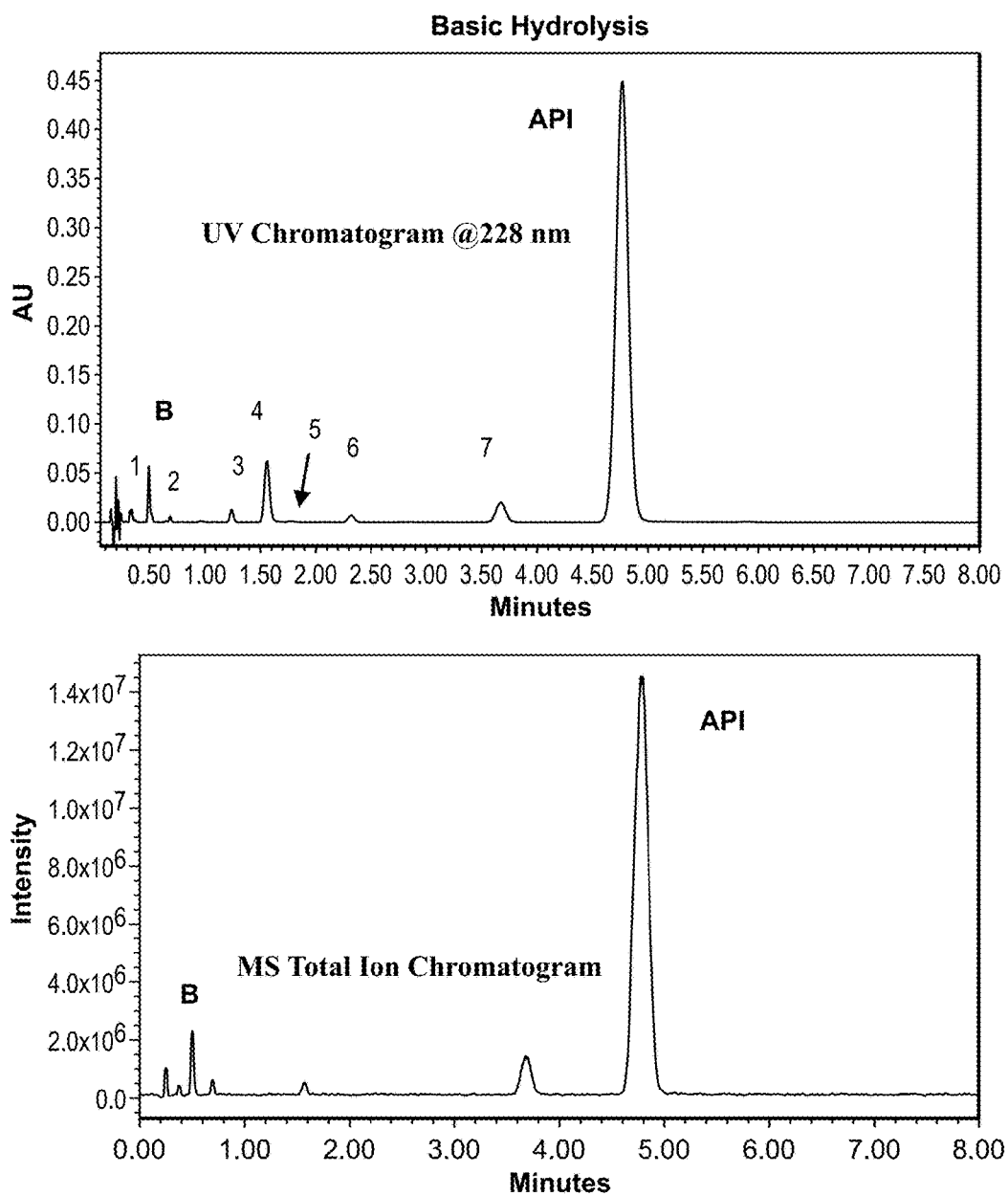
FIG. 20 includes chromatograms of base hydrolysis of the glimepiride drug substance at 1 days. The sample degraded to several degradation products. While both related compound B (B) is present, numerous additional products were also formed.
Figure 21:
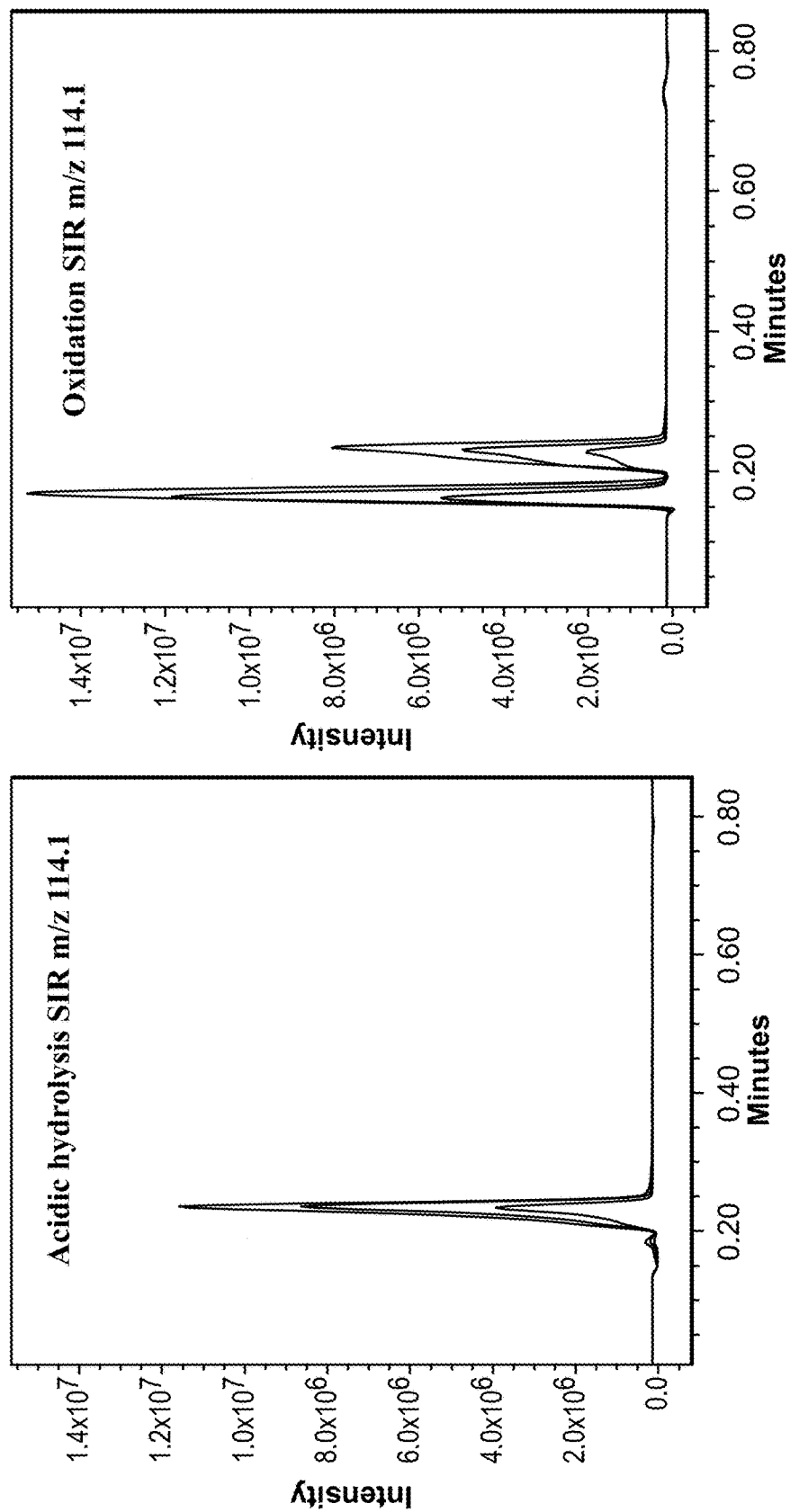
FIG. 21 includes mass spectrum Single Ion Rerecording channel (SIR) m/z 114.1 of acidic hydrolysis (left) and oxidation (right) of the glimepiride drug substance. Acidic hydrolysis produces a single isomer, which increases in peak area over time. Oxidation produced two isomers, also increasing in area with time.

Under basic hydrolysis conditions, the drug substance degraded rapidly, over a period of 1 day with >10% of degradation. FIG. 20 shows chromatograms from the glimepiride drug substance after base hydrolysis for one day. In contrast to the previously described analyses, many smaller impurity peaks were observed. A peak corresponding to related compound B was present at 1.83% peak area, however, related compound C, based on retention time and expected mass spectral data was not observed. Additional predominant degradation peaks were found as shown in the table below.

Impurity Peaks Found in Base Hydrolysis

| Compound (#) | Retention Time | % Area | Base m/z |
|---|---|---|---|
| RRT 0.07 (1) | 0.34 | 0.58 | 138.1 |
| Related compound B | 0.49 | 1.83 | 374.4 |
| RRT 0.144 (2) | 0.69 | 0.23 | 461.5 |
| RRT 0.260 (3) | 1.24 | 0.71 | 420.4 |
| RRT 0.327 (4) | 1.57 | 5.13 | 545.3 |
| RRT 0.372 (5) | 1.77 | 0.10 | 543.5 |
| RRT 0.49 (6) | 2.32 | 0.68 | 543.7 |
| RRT 0.77 (7) | 3.67 | 3.09 | 527.5 |

In summary, under acidic hydrolysis conditions, the formation of two additional peaks were observed by UV. These peaks were found to increase over the time period with 9.72% impurities achieved at 5 days (see FIG. 17). A similar pattern was observed for the oxidative degradation conditions as well with 8.53% impurities at 5 days (see FIG. 19). Under basic hydrolysis conditions, a greater number of peaks were observed by UV (see FIG. 20). In addition, under basic hydrolysis, the rate of degradation was substantially faster than that observed under acidic hydrolysis or oxidative conditions. Under basic hydrolysis, the target amount of impurities was achieved at 1 day, with over 10% impurities formed.

Mass balance calculations were performed using the experimentally determined RRFs for acidic, oxidative and basic degradation conditions. The results show the impact of recovery with and without the use of relative response factors. Both the % impurity and recovery were impacted similarly, however, the implications for % impurity are greater, in that impurity reporting, identification and qualification thresholds can be impacted by as little as 0.05%.

Although the target degradation was approximately 10%, values are shown for all the time points. All of the recoveries are slightly higher without adjusting for the difference in relative response of the impurities and the API. This is expected given the response of both related compound B and C were higher than at for glimepiride.

Under acidic hydrolysis conditions, the percent of impurities increased with time with degradation of 19.55% at 7 days as shown in the table below.

Analysis of Degradation of Drug Substance Under Acidic Hydrolysis Conditions

| Time (days) | % Impurities | % Impurities with RRF | Recovery (%) | Recovery (%) (with RRF) |
|---|---|---|---|---|
| 1 | 2.35 | 1.95 | 98.97 | 98.68 |
| 3 | 6.13 | 5.14 | 101.07 | 100.14 |
| 5 | 9.67 | 8.15 | 99.50 | 97.98 |
| 7 | 19.55 | 16.69 | 103.56 | 100.12 |

By accounting for the difference in response factor both the % impurity and the recovery decreased with the difference at 7 days of approximately 3%. In other words, impurities were over represented by 3% without taking into account RRF.

Calculations for mass balance and % impurity for the oxidation studies, gave similar results to those observed with acidic hydrolysis, albeit, a slightly lower rate of degradation as compared to the acidic hydrolysis conditions as shown in the table below.

Analysis of Degradation of Drug Substance Under Oxidative Conditions

| Time (days) | % Impurities | % Impurities with RRF | Recovery (%) | Recovery (%) with RRF |
|---|---|---|---|---|
| 1 | 1.75 | 1.45 | 101.07 | 100.88 |
| 3 | 4.83 | 4.05 | 101.75 | 101.05 |
| 5 | 7.45 | 6.28 | 98.30 | 97.21 |
| 7 | 9.95 | 8.42 | 98.39 | 96.88 |

Over the 7 day period the amount of impurities increased to 9.95% at 7 days and a decrease in recoveries also observed. Using RRF's resulted in lower recoveries and % impurities than assuming a RRF of 1, with difference of up to 1.5%, at 7 days.

Basic hydrolysis conditions resulted in the greatest number of impurities, as well as the highest rate of degradation. The RRF for related compound B and C had a minimal effect on the % impurity and recovery calculations, since the proportion of these impurities to the total was low. At 1 day, a difference on 0.5% was observed when accounting for relative response as shown in the table below.

Analysis of Degradation of Drug Substance Under Basic Hydrolysis Conditions

| Time (days) | % Impurities | % Impurities with RRF | Recovery (%) | Recovery (%) with RRF |
|---|---|---|---|---|
| 1 | 12.45 | 11.99 | 99.21 | 98.81 |
| 3 | 33.45 | 31.59 | 88.60 | 86.30 |
| 5 | 54.68 | 51.92 | 82.00 | 77.38 |

The impact of the RRF increased to 3% at 5 days, however, at this point over 50% degradation had occurred. Given the large number of impurities, the impact of applying the RRF for related compound B, solely, was significantly less than observed for acidic and oxidative condition. Extensive degradation resulted in significantly lower recoveries, likely due to the large number of impurities and each compounds RRF, as well as products with no chromophore or immeasurable by UV.

Mass detection was employed for confirmation of the degradation pathway and to reconcile mass balance differences. During the formation of both related compound B and related compound C, there is a loss of 4-methylcyclohexylamine (see FIG. 14). Since 4-methylcyclohexylamine does not contain a chromophore, the presence of a mass detector enabled not only identification but also quantitation of the by-product.

Quantitation of 4-methylcyclohexylamine was achieved utilizing standards prepared from commercially available reagents. Working standards were prepared to cover the range from 0.04 to 10% (0.1 to 25 ug/mL). A single ion recording channel measuring the response for m/z=114.1 Da was used for quantitation. The working standard was present as a mixture of both the cis and trans geometric isomers. These isomers were partially separated chromatographically, therefore the sum of the isomers was used for the calibration curve. The calibration curve was quadratic and converted to a linear relationship using a log-log fit over the desired quantitation range with the parameters listed in the following table.

Calibration Curve Data for
4-methylcylcohexylamine by MS

| Component | n | fit | weighting | y intercept | slope | $R^2$ |
|---|---|---|---|---|---|---|
| Sum of cis- and trans-isomers | 5 | Log-log line: | none | 6.77 | 0.835 | 0.997563 |

Using the calibration curve, 4-methylcylcohexylamine was quantified in the acidic and oxidative degradation reactions over the period of 5 days. The results, which are listed in the table below, showed an increase in the level of the by-product with impurity formation.

4-methylcylohexylamine (4-MeCHA) Quantitation
Under Acidic Degradation Conditions

| Time (days) | % Impurities (with RRF) | 4-MeCHA (μg/mL) (%) | Recovery (%) (with RRF) | Recovery (%) + 4-MeCHA |
|---|---|---|---|---|
| 1 | 1.95 | 0.36 (0.14%) | 98.68 | 98.82 |
| 3 | 5.14 | 0.98 (0.39%) | 100.14 | 100.53 |
| 5 | 8.15 | 1.74 (0.70%) | 97.98 | 98.68 |

As shown in the table above, the amount of 4-methylcylcohexylamine formed under acidic hydrolysis conditions increased over the time period. The recoveries previously calculated increased from 0.2-1.1%. The quantitation of the by-product formed in the reaction allows a more accurate evaluation of the mass balance of the reaction.

Figure 18:
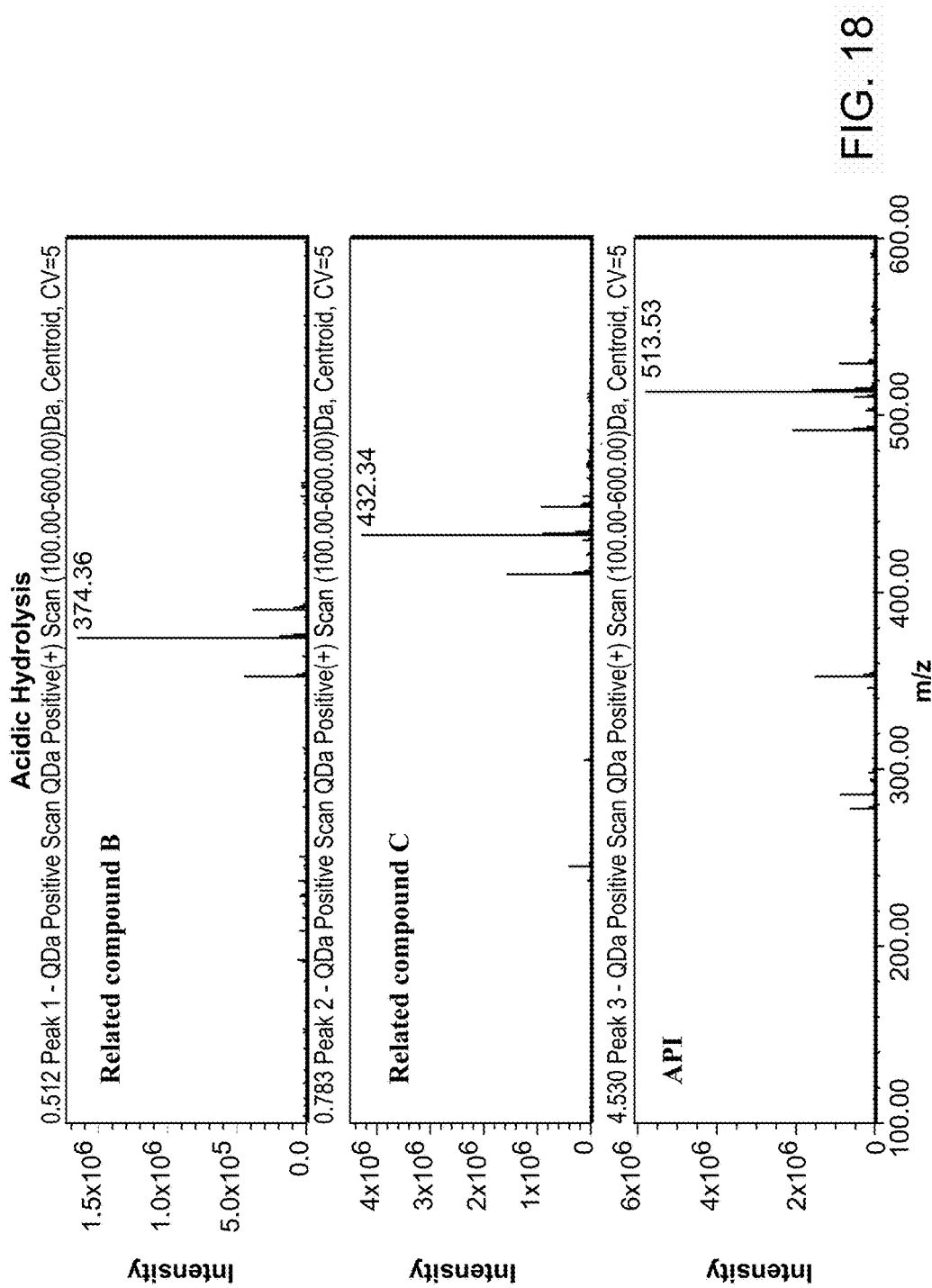
FIG. 18 includes spectra of peaks in MS, Total Ion Chromatogram (TIC) for related compounds B (top), C (middle) and API (bottom) under acid hydrolysis of glimepiride drug substance at 5 days. Impurities and the API were predominantly present as Na+ adducts under the conditions used for the analysis.

Similar results were obtained under oxidative conditions, however unlike acidic conditions, both isomers of 4-methylcylcohexylamine were formed (see FIG. 18). Because glimepiride is a trans-isomer, the results suggest a number of possibilities. For example, the drug substance may also contain the cis-isomer of glimepiride or related. Alternatively, during oxidation by the radical generator AIBN, there may be a conversion of 4-methylcylcohexylamine from the trans- to the cis-isomer. Regardless, the acidic hydrolysis reaction appears to be stereoselective while oxidation by radical generator is not.

Conclusions

The use of multi detection including UV, ELSD, and MS enabled for additional techniques for both RRF determinations as well as mass balance calculations. The determination of RRF using a UV detector in combination with a mass sensitive detector, such as ELS, enabled the RRF value to be estimated in a single analysis without requiring analysis of separate calibration samples. The correlation with values achieved using a conventional calibration curve technique is highest when compounds with similar response in ELS are present in equal amounts, which is partially due to the limited sensitivity of the ELS detector.

Mass balance determinations may be more accurate using multi-detection techniques. Applying RRF values to forced degradations impacts mass balance, particularly for those impurities that either are present in greater amounts (>0.5%) or have a significantly different response factor in UV (<0.8 or >1.2). In addition, MS can be used to quantify or evaluate non-chromophoric compounds for a more comprehensive understanding of the mass balance in forced degradations.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. Still further, the components and methods identified in the Background section are integral to this disclosure and can be used in conjunction with or substituted for components and methods described elsewhere in the disclosure within the scope of the invention.

The invention claimed is:

1. A method for determining relative response factors comprising:
    performing liquid chromatographic separation of a sample including a reference compound and one or more additional compounds;
    performing molar concentration-based detection on the separated sample to determine a molar-based peak area for the reference compound and for each of the one or more additional compounds;
    performing mass concentration-based detection on the separated sample to determine a mass-based peak area for the reference compound and for each of the one or more additional compounds; and
    determining a relative response factor (RRF) for each of the one or more additional compounds based on the ratio of the molar-based peak area for the additional compound to the logarithm of the mass-based peak area for the additional compound and the ratio of the molar-based peak area for the reference compound to the logarithm of the mass-based peak area for the reference compound.

2. A method for determining relative concentrations of a reference compound and one or more additional compounds in a test sample, the method comprising:
    determining relative response factors for the one or more additional compounds using the method of claim 1;
    performing liquid chromatographic separation of the test sample;
    performing molar concentration-based detection on the separated test sample to determine a molar-based peak area for the reference compound and for each of the one or more additional compounds;

applying the relative response factor for an additional compound to the molar-based peak area for the additional compound to obtain a corrected molar-based peak area for each of the one or more additional compounds in the test sample; and determining the relative concentrations of the reference compound and the one or more additional compounds in the test sample based on the molar-based peak area of the reference compound and on the corrected molar-based peak area for each additional compound.

3. The method of claim 2, wherein the sample used to determine the relative response factors is the same as the test sample.

4. A method for determining concentrations of a reference compound and one or more additional compounds in a test sample, the method comprising:

determining relative response factors for the one or more additional compounds using the method of claim 1;

performing liquid chromatographic separation of the test sample;

performing molar concentration-based detection on the separated test sample to determine a molar-based peak area for the reference compound and for each of the one or more additional compounds;

applying the relative response factor for an additional compound to the molar-based peak area for the additional compound to obtain a corrected molar-based peak area for each additional compound in the test sample;

determining the relative concentrations of the reference compound and the one or more additional compounds in the test sample based on the molar-based peak area of the reference compound and the corrected molar-based peak area for each additional compound;

performing liquid chromatographic separation of a reference sample including a known concentration of the reference compound;

performing molar concentration-based detection on the reference sample to determine a molar-based peak area for the reference compound in the reference sample; and comparing the molar-based peak area of the reference compound in the reference sample to the molar-based peak area of reference compound in the test sample to obtain concentrations of the reference compound and the one or more additional compounds in the test sample from the determined relative concentrations of the reference compound and one or more additional compounds in the test sample.

5. A method of performing mass balance for a degraded sample including an active pharmaceutical ingredient (API) and one or more impurities, the method comprising:

determining relative response factors for the one or more impurities using the method of claim 1 with the reference compound being the API and the one or more additional compounds being the one or more impurities;

performing liquid chromatographic separation of an initial sample not subjected to degrading conditions;

performing molar concentration-based detection on the separated initial sample to determine a molar-based peak area for the API and for each of the one or more impurities in the initial sample;

applying the relative response factor for each of the one or more impurities to the molar-based peak area for the impurity to obtain a corrected molar-based peak area for each impurity in the initial sample;

performing liquid chromatographic separation of a degraded test sample, the degraded test sample being a test sample including the API that was previously subjected to degrading conditions;

performing molar concentration-based detection on the separated degraded test sample to determine a molar-based peak area for the API and for each of the one or more impurities;

applying the relative response factor for an impurity to the molar-based peak area for the impurity to obtain a corrected molar-based peak area for each of the one or more impurities in the degraded test sample; and comparing the sum of the corrected molar-based peak areas of the one or more impurities and the molar-based peak area of the API for the degraded sample with the sum of the corrected molar-based peak areas the one or more impurities and the molar-based peak area of the API for the initial sample to obtain a percentage recovery.

6. The method of claim 1, wherein the relative response factor for each of the one or more additional compounds ($RRF_{add\_cpnd}$) is a function of the ratio of the molar-based peak area for the additional compound ($Molar\_Area_{add\_cpnd}$) to the logarithm of the mass-based peak area for the additional compound ($\log(Mass\_Area_{add\_cpnd})$) divided by the ratio of the molar-based peak area for the reference compound ($Molar\_Area_{add\_cpnd}$) to the logarithm of the mass-based peak area for the reference compound ($\log(Mass\_Area_{add\_cpnd})$).

7. The method of claim 6, wherein the relative response factor for each of the one or more additional compounds is described by the following equation:

$$RRF_{add\_cpnd} \propto \frac{Molar\_Area_{add\_cpnd}}{\log(Mass\_Area_{add\_cpnd})} \Big/ \frac{Molar\_Area_{ref\_cmpd}}{\log(Mass\_Area_{ref\_cmpd})}.$$

8. The method of claim 1, wherein the molar concentration-based detection is absorption spectroscopy in the ultraviolet-visible spectral region.

9. The method of claim 1, wherein the mass concentration-based detection is evaporative light scattering detection (ELSD).

10. The method of claim 1, wherein the liquid chromatographic separation includes high performance liquid chromatography.

11. The method of claim 1, wherein the chromatographic separation includes ultra-high performance liquid chromatography (UHPLC).

12. The method of claim 1, wherein the reference compound is an active pharmaceutical ingredient (API) and the one or more additional compounds are one or more impurities.

13. The method of claim 1, wherein the chromatographic separation is isocratic.

14. A method for determining relative concentrations of an active pharmaceutical ingredient (API) and one or more impurities in a test sample, the method comprising:

determining relative response factors for the one or more related impurities using the method of claim 1 with the reference compound being the API, the one or more additional compounds being the one or more impurities, the molar concentration-based detection being absorbance-based detection, and the mass concentration-based detection being evaporative light scattering detection (ELSD);
performing liquid chromatographic separation of the test sample;
performing absorbance detection on the separated test sample to determine an absorbance peak area for the API and for each of the one or more related impurities;
applying the relative response factor for an impurity to the absorbance peak area for the impurity to obtain a corrected absorbance peak area for each of the one or more impurities in the test sample; and
determining the relative concentrations of the API and the one or more impurities in the test sample based on the absorbance peak of the API and on the corrected absorbance peak area for each impurity.

15. A method for determining concentrations of an active pharmaceutical ingredient (API) and one or more related impurities in a test sample, the method comprising:
determining relative response factors for the one or more related impurities using the method of claim 1 with the reference compound being the API, the one or more additional compounds being the one or more impurities, the molar concentration-based detection being absorbance-based detection, and the mass concentration-based detection being evaporative light scattering detection (ELSD);
performing liquid chromatographic separation of the test sample;
performing absorbance detection on the separated test sample to determine an absorbance peak area for the API and for each of the one or more related impurities;
applying the relative response factor for an impurity to the absorbance peak area for the impurity to obtain a corrected absorbance peak area for each of the one or more impurities in the test sample;
performing liquid chromatographic separation of a reference sample including a known concentration of the API;
performing absorbance detection on the reference sample to determine an absorbance peak area for the API in the reference sample; and
comparing the absorbance peak area of the API in the reference sample to the absorbance peak area of API in the test sample to obtain concentrations of the API and the one or more related impurities in the test sample from the determined relative concentrations of the API and one or more related impurities in the test sample.

16. A method for determining relative response factors comprising:
performing liquid chromatographic separation of a first sample including a reference compound;
performing molar concentration-based detection on the separated first sample to determine a molar-based peak area for the reference compound;
performing mass concentration-based detection on the separated first sample to determine a mass-based peak area for the reference compound;
performing liquid chromatographic separation of a second sample including one or more additional compounds;
performing molar concentration-based detection on the separated second sample to determine a molar-based peak area for each of the one or more additional compounds;
performing mass-based detection on the separated second sample to determine a mass-based peak area for each of the one or more additional compounds; and
determining a relative response factor (RRF) for each of the one or more additional compounds based on the ratio of the molar-based peak area for the additional compound to the logarithm of the mass-based peak area for the additional compound and the ratio of the molar-based peak area for the reference compound to the logarithm of the mass-based peak area for the reference compound.

17. A method for determining relative concentrations of a reference compound and one or more additional compounds in a test sample, the method comprising:
determining relative response factors for the one or more additional compounds using the method of claim 16;
performing liquid chromatographic separation of the test sample;
performing molar concentration-based detection on the separated test sample to determine a molar-based peak area for the reference compound and for each of the one or more additional compounds;
applying the relative response factor for an additional compound to the molar-based peak area for the additional compound to obtain a corrected molar-based peak area for each of the one or more additional compounds in the test sample; and
determining the relative concentrations of the reference compound and the one or more additional compounds in the test sample based on the molar-based peak area of the reference compound and on the corrected molar-based peak area for each additional compound.

18. A method of performing mass balance for a degraded sample including an active pharmaceutical ingredient (API) and one or more impurities, the method comprising:
determining relative response factors for the one or more impurities using the method of claim 16 with the reference compound being the API and the one or more additional compounds being the one or more impurities;
performing liquid chromatographic separation of an initial sample not subjected to degrading conditions;
performing molar concentration-based detection on the separated initial sample to determine a molar-based peak area for the API and for each of the one or more impurities in the initial sample;
applying the relative response factor for each of the one or more impurities to the molar-based peak area for the impurity to obtain a corrected molar-based peak area for each impurity in the initial sample;
performing liquid chromatographic separation of a degraded test sample, the degraded test sample being a test sample including the API that was previously subjected to degrading conditions;
performing molar concentration-based detection on the separated degraded test sample to determine a molar-based peak area for the API and for each of the one or more impurities;
applying the relative response factor for an impurity to the molar-based peak area for the impurity to obtain a corrected molar-based peak area for each of the one or more impurities in the degraded test sample; and
comparing the sum of the corrected molar-based peak areas of the one or more impurities and the molar-based peak area of the API for the degraded sample with the sum of the corrected molar-based peak areas the one or more impurities and the molar-based peak area of the API for the initial sample to obtain a percentage recovery.

19. The method of claim 16, wherein the relative response factor for each of the one or more additional compounds ($RRF_{add\_cpnd}$) is a function of the ratio of the molar-based peak area for the additional compound ($Molar\_Area_{add\_cpnd}$) to the logarithm of the mass-based peak area for the additional compound ($\log(Mass\_Area_{add\_cpnd})$) divided by the ratio of the molar-based peak area for the reference compound ($Molar\_Area_{add\_cpnd}$) to the logarithm of the mass-based peak area for the reference compound ($\log(Mass\_Area_{add\_cpnd})$).

20. The method of claim 19, wherein the relative response factor for each of the one or more impurities is described by the following equation:

$$RRF_{add\_cpnd} \propto \frac{Molar\_Area_{add\_cpnd}}{\log(Mass\_Area_{add\_cpnd})} \Big/ \frac{Molar\_Area_{ref\_cmpd}}{\log(Mass\_Area_{ref\_cmpd})}.$$

21. A system comprising:
a liquid chromatography column configured to perform liquid chromatographic separation of a sample including a reference compound and one or more additional compounds;
a molar concentration-based detector;
a mass concentration-based detector;
a molar concentration-based detection module executed by a processor in a processing device and configured to perform molar concentration-based detection on the separated sample, using the molar concentration-based detector, to determine a molar-based peak area for the reference compound and for each of the one or more additional compounds;
a mass concentration-based detection module executed by the processor and configured to perform mass concentration-based detection on the separated sample, using the mass concentration-based detector, to determine a mass-based peak area for the reference compound and for each of the one or more additional compounds; and
a relative response factor module executed by the processor and configured to:
compute a first ratio of the molar-based peak area for the additional compound to a logarithm of the mass-based peak area for the additional compound;
compute a second ratio of the molar-based peak area for the reference compound to a logarithm of the mass-based peak area for the reference compound; and
compute a relative response factor for each of the one or more additional compounds based on the first ratio and the second ratio.

22. The system of claim 21, further comprising:
a mass balance module executed by the processor and configured to determine a mass balance in the sample based on the molar-based peak areas for the reference compound and for each of the one or more additional compounds, and the relative response factors for each of the one or more additional compounds.

23. A system comprising:
a liquid chromatography column configured to perform liquid chromatographic separation of a sample including a reference compound and one or more additional compounds;
a molar concentration-based detector;
a mass concentration-based detector;
a chromatography control module executed by one or more processors in a processing device and configured to control liquid chromatographic separation of the sample including the reference compound and the one or more additional compounds using h liquid chromatography column;
a molar concentration-based detection module executed by the one or more processors and configured to control molar concentration-based detection on the separated sample using the molar concentration-based detector and configured to determine a molar-based peak area for the reference compound and for each of the one or more additional compounds;
a mass concentration-based detection module executed by the one or more processors and configured to control mass concentration-based detection on the separated sample using the mass concentration-based detector and configured to determine a mass-based peak area for the reference compound and for each of the one or more additional compounds; and
a relative response factor module executed by the one or more processors and configured to:
compute a first ratio of the molar-based peak area for the additional compound to a logarithm of the mass-based peak area for the additional compound;
compute a second ratio of the molar-based peak area for the reference compound to a logarithm of the mass-based peak area for the reference compound; and
compute a relative response factor for each of the one or more additional compounds based on the first ratio and the second ratio.

24. The system of claim 23, further comprising:
a mass balance module executed by the one or more processors and configured to determine a mass balance in the sample based on the molar-based peak areas in the sample for the reference compound and for each of the one or more additional compounds, and the relative response factors for each of the one or more additional compounds.

* * * * *